US011672268B2

(12) United States Patent
Kozubal et al.

(10) Patent No.: US 11,672,268 B2
(45) Date of Patent: Jun. 13, 2023

(54) EDIBLE FOODSTUFFS AND BIO REACTOR DESIGN

(71) Applicant: The Fynder Group, Inc., Chicago, IL (US)

(72) Inventors: Mark A. Kozubal, Bozeman, MT (US); Richard E. Macur, Manhattan, MT (US); Yuval C. Avniel, Missoula, MT (US); Maximilian Devane Hamilton, Bozeman, MT (US)

(73) Assignee: The Fynder Group, Inc., Chicago, IL (US)

( * ) Notice: Subject to any disclaimer, the term of this patent is extended or adjusted under 35 U.S.C. 154(b) by 0 days.

(21) Appl. No.: 17/891,857

(22) Filed: Aug. 19, 2022

(65) Prior Publication Data

US 2022/0400726 A1 Dec. 22, 2022

Related U.S. Application Data

(63) Continuation of application No. 16/116,836, filed on Aug. 29, 2018, now Pat. No. 11,464,251.

(Continued)

(51) Int. Cl.

*A23L 31/00* (2016.01)
*A23J 3/22* (2006.01)

(Continued)

(52) U.S. Cl.

CPC ............ *A23L 31/00* (2016.08); *A23C 9/1203* (2013.01); *A23G 9/36* (2013.01); *A23J 3/20* (2013.01);

(Continued)

(58) Field of Classification Search

CPC ........ A23L 31/10; A23L 29/065; A23J 3/227; C12M 1/00; C12M 23/24; C12M 23/40;

(Continued)

(56) References Cited

U.S. PATENT DOCUMENTS 2,450,055 A * 9/1948 Nord ........................ A23J 3/20 426/72
4,265,915 A * 5/1981 MacLennan ........... A01G 18/20 435/933

(Continued)

FOREIGN PATENT DOCUMENTS

CN 107205457 9/2017
DE 102007061256 6/2009

(Continued)

OTHER PUBLICATIONS

"Scoby Puree," Cultured Food Life, Aug. 26, 2016, retrieved from https://www.culturedfoodlife.com/recipe/scoby-puree/, 2 pages.

(Continued)

*Primary Examiner* — Hamid R Badr

(74) *Attorney, Agent, or Firm* — Sheridan Ross P.C.

(57) ABSTRACT

Methods of production of edible filamentous fungal biomat formulations are provided as standalone protein sources and/or protein ingredients in foodstuffs as well as a one-time use or repeated use self-contained biofilm-biomat reactor comprising a container with at least one compartment and placed within the compartment(s), a feedstock, a fungal inoculum, a gas-permeable membrane, and optionally a liquid nutrient medium.

28 Claims, 14 Drawing Sheets

Related U.S. Application Data

(60) Provisional application No. 62/722,074, filed on Aug. 23, 2018, provisional application No. 62/552,093, filed on Aug. 30, 2017.

(51) Int. Cl.

| | |
|---|---|
| ***A23L 29/00*** | (2016.01) |
| ***C12N 1/14*** | (2006.01) |
| ***C12M 1/00*** | (2006.01) |
| ***C12M 1/04*** | (2006.01) |
| ***A23L 33/195*** | (2016.01) |
| ***A23C 9/12*** | (2006.01) |
| ***A23G 9/36*** | (2006.01) |
| ***A23J 3/20*** | (2006.01) |
| *C12R 1/77* | (2006.01) |

(52) U.S. Cl.

CPC ............. *A23J 3/227* (2013.01); *A23L 29/065* (2016.08); *A23L 33/195* (2016.08); *C12M 21/00* (2013.01); *C12M 23/24* (2013.01); *C12M 23/34* (2013.01); *C12M 23/40* (2013.01); *C12N 1/14* (2013.01); *C12N 1/145* (2021.05); *A23V 2002/00* (2013.01); *A23V 2250/208* (2013.01); *C12R 2001/77* (2021.05)

(58) Field of Classification Search

CPC . C12N 1/14; A23V 2002/00; A23V 2250/208

USPC ............................................................ 426/60

See application file for complete search history.

(56) References Cited

U.S. PATENT DOCUMENTS

| | | | |
|---|---|---|---|
| 2004/0197461 | A1 | 10/2004 | Finnigan et al. |
| 2022/0400726 | A1 | 12/2022 | Kozubal et al. |
| 2022/0408776 | A1 | 12/2022 | Kozubal et al. |

FOREIGN PATENT DOCUMENTS

| | | |
|---|---|---|
| GB | 1440642 | 6/1976 |
| GB | 2535864 | 1/2021 |
| IL | 253279 | 9/2017 |
| WO | WO 02/090527 | 11/2002 |
| WO | WO 2016/004380 | 1/2016 |

OTHER PUBLICATIONS

"Scoby Smoothie," Cultured Food Life, Aug. 30, 2016, retrieved from https://www.culturedfoodlife.com/recipe/scoby-smoothie/, 2 pages.

Christensen, "How to Make Your Own Kombucha Scoby: Cooking Lessons from the Kitchn," The Kitchn, published Apr. 24, 2014, archived webpage dated Jul. 22, 2015 and retrieved from https://web.archive.org/web/20150722021028/https://www.thekitchn.com/how-to-make-your-own-kombucha-scoby-cooking-lessons-from-the-kitchn-202596, 6 pages.

Ma et al., "Preparation and characteristics of biodegradable mulching films based on fermentation industry wastes," International Biodeterioration and Biodegradation, vol. 111, Apr. 28, 2016, pp. 54-61.

Notice of Allowance for U.S. Appl. No. 16/116,836, dated May 9, 2022, 9 pages.

Notice of Allowance for U.S. Appl. No. 17/095,724, dated Dec. 9, 2021 9 pages.

Official Action for U.S. Appl. No. 17/882,490, dated Oct. 24, 2022, 7 pages.

Official Action for U.S. Appl. No. 17/891,873, dated Nov. 7, 2022, 11 pages.

Official Action for U.S. Appl. No. 17/959,495, dated Jan. 19, 2023, 6 pages.

Decision on Appeal for U.S. Appl. No. 16/442,188, dated Feb. 25, 2022, 27 pages.

Official Action for U.S. Appl. No. 16/442,188, dated Jun. 8, 2022, 12 pages.

Official Action for U.S. Appl. No. 16/442,188, dated Nov. 18, 2022, 14 pages.

Notice of Allowance for U.S. Appl. No. 17/882,490, dated Feb. 14, 2023, 9 pages.

Notice of Allowance for U.S. Appl. No. 17/891,873, dated Mar. 2, 2023, 8 pages.

* cited by examiner

EDIBLE FOODSTUFFS AND BIO REACTOR DESIGN

CROSS-REFERENCE TO RELATED APPLICATIONS

This application is a continuation of U.S. patent application Ser. No. 16/116,836, filed 29 Aug. 2018, which claims the benefit of priority of U.S. Provisional patent applications 62/722,074, filed 23 Aug. 2018, and 62/552,093, filed 30 Aug. 2017. The entireties of all of the above-referenced applications are incorporated herein by reference.

STATEMENT REGARDING FEDERALLY SPONSORED RESEARCH

This invention was made with government support under Small Business Technology Transfer (STTR) program grant numbers STTR NASA 80NSSC20C0031 and STTR NASA 80NSSC18P2141 awarded by the National Aeronautics and Space Administration. The government has certain rights in the invention.

TECHNICAL FIELD

This application relates to edible fungi and provides methods of preparing edible fungi for use in foodstuffs, liquid and solid formulations of edible fungi, as well as uses and methods associated therewith, foodstuffs containing edible fungi, and methods and uses thereof.

BACKGROUND

The United Nations listed the world population as 7.5 billion in August 2017 and predicts that figure to grow to 8 billion in 2023 and to be 10 billion in 2056. In a related report, the Food and Agricultural Organization of the United Nations (FAO) estimates that if the global population reaches 9.1 billion by 2050, world food production will need to rise by 70% and to double in the developing world. That increase in food production will need to occur despite rising energy costs, decreasing underground aquifer resources, loss of farm land to urban sprawl, and increasingly severe weather due to climate change (e.g. increased temperatures, increased drought, increased flooding, etc.). This is a particular challenge for countries such as Africa which, according to 2009 figures, already has inadequate protein intake and countries such as China, India, Pakistan, and Indonesia which are at risk of inadequate protein intake. In addition, the global demand is forecasted for 2040 to increase by 60% for meat and 50% for dairy.

But not all protein sources are created equal. Animal based foods (meat, eggs, dairy) provide "complete" proteins as they contain all of the essential amino acids; that is, methionine, leucine, isoleucine, phenylalanine, valine, threonine, histidine, tryptophan and lysine. Plant based foods, while containing some essential amino acids, generally lack the complete set. For example, the protein found in starchy roots lacks the essential amino acid lysine, which must then be obtained from another food in the diet. Beans and legumes contain high levels of lysine, but they lack the essential amino acid methionine. Although it is possible to build a complete protein by pairing plant foods, ensuring a nutritionally balanced diet is much easier with complete proteins.

One non-animal source of a complete protein is obtained from edible filamentous fungi, such as *Fusarium venenatum* (formerly classified and *Fusarium graminearum*). However, to date protein production from these sources has required significant investment in energy resources and production equipment, such as capital-intensive bioreactors and centrifuges. There remains a need for growth, harvesting, and foodstuff production methods that require low energy, consume few natural resources, and are low cost. The current invention solves these problems.

In addition, one area of reducing the logistics supply associated with responding to natural disasters, logistically isolated environments or military and/or space/extraterrestrial missions is the closure of life support loops, particularly waste streams, while providing mission critical products such as nutritional and appetizing foods, fuels, metabolite expression platforms, building materials and/or microbial factories. Oftentimes these types of environments have no or limited access to sterile facilities and/or require a sealed aseptic system to fully contain the waste stream and/or food, fuel and materials produced. For example, work by the European Space Agency (Expeditions 25-28, Growth and Survival of Colored Fungi in Space (CFS-A)) demonstrated that fungi can grow inside the space station and could decompose food and other organic materials in humid conditions; here containment of the fungal system is paramount to preventing inadvertent contamination of other supplies and surfaces. In addition to the need to decompose food and waste in the developing area of space travel, these needs are also present when dealing with natural disasters, in-theater military operations, wilderness operations, situations in the third world where sanitation and refrigeration are not reliable, confined spaces, logistically difficult arenas and in some agricultural/industrial operations. Having a self-contained aseptic system that operates efficiently with a minimum of space, energy, and maintenance is needed.

A robust and efficient portable self-contained biofilm-biomat reactor system that is able to convert a wide variety of waste streams into a multitude of valuable products addresses these problems. The current disclosure describes a simple aseptic bioreactor platform that requires no agitation, no active aeration, no energy source during fermentation (other than temperature control), generates minimal to no waste residues, requires little water, and produces dense, easily harvested, textured biomats. In addition, the self-contained biofilm-biomat reactor system can be portable and/or scalable for larger, more concentrated missions and/or populations.

SUMMARY

The present disclosure provides formulations of edible filamentous fungi. The edible filamentous fungi are grown on liquid media under surface fermentation conditions to produce filamentous fungal biomats. In one embodiment, a method for surface fermentation production of edible fungal biomats is provided, the method comprising inoculating a liquid synthetic growth media containing a carbon source with planktonic and/or microconidial fungal cells, incubating the inoculated growth media at room temperature and harvesting a cohesive biomat produced by the fungus. In some embodiments the inoculated growth media is incubated in open trays or in open trays contained in at least a semi-sterile environment In another embodiment, the production method for surface fermentation edible fungal biomat production allows harvesting a section of the biomat while maintaining the growth potential of the remaining biomat.

In a further embodiment, the filamentous fungus is *Fusarium oxysporum* strain MK7 (ATCC PTA-10698 deposited with the American Type Culture Collection, 1081 University Boulevard, Manassas, Va., USA), which has 46-51% complete protein content with high levels of all essential amino acids, specifically, 42-43% essential amino acids and 4-21% BCAA, which is higher than eggs. In addition, *Fusarium oxysporum* strain MK7 has a 8-10% minerals and ash content, including high levels of Calcium (1.3 mg/100 g serving), Iron (5.5 mg/100 g serving), 1-2% nucleic acid, and 6-11% lipid, of which 85% is unsaturated.

In another embodiment, the filamentous fungus is *Fusarium venenatum* or *Fusarium fujikuroi.*

In still another embodiment, the filamentous fungus is selected from the group consisting of *Agaricus bisporus* (crimini and white), *Boletus edulis* (porcinini), *Cantarellus cibarius* (chantrelle), *Calvatia gigantea* (giant puffball), *Cyclocybe aegerita* (velvet piopinni), *Ganoderma lucidum* (Reishi), *Grifola frondosa* (maitake), *Morchella* species (Morel), *Hypsizygus tessellatus* (clamshell), *Hypsizygus ulmarius* (elm oyster), *Laetiporus* species (chicken of the woods), *Lentinula edodes* (shiitake), *Pleurotus eryngii* (trumpet royale, king oyster), *Calvatia gigantean* (giant puffball), *Pleurotus ostreatus* (pearl oyster), *Pleurotus ostreatus* var. columbinus (blue oyster) and other *Pleurotus* sp. (e.g., *P. citrinopileatus, tuberregium*), *Hypsizygus ulmarius* (elm oyster), *Pholiota microspora* (forest nameko), *Sparassis crispa* (cauliflower), and *Tuber* species (truffles).

In an additional embodiment, the carbon source is a sugar (e.g. sucrose, maltose, glucose, fructose, rare sugars, etc.), a sugar alcohol (e.g. glycerol, polyol, etc.), a starch (e.g. corn starch, etc.), a starch derivative, a starch hydrolysate, a hydrogenated starch hydrolysate, a lignocellulosic pulp or feedstock (e.g. sugar beet pulp, agricultural pulp, lumber pulp, distiller dry grains, brewery waste, etc.), corn steep liquor, acid whey, sweet whey, milk serum, wheat steep liquor, industrial liquor, food refinery products/waste streams, and/or combinations thereof.

In yet another embodiment, a method for surface fermentation production of edible filamentous fungal biomats initiated from the fruiting bodies or spores of filamentous fungi is provided. For biomats initiated from fruiting bodies, the method comprises surface sterilizing the fruiting body of the fungus, reducing the size of the sterilized fruiting body of the fungus, surface sterilizing the reduced fruiting body of the fungus, inoculating a synthetic liquid growth media containing a carbon source with cells from the sterilized reduced fruiting body of the fungus, incubating the inoculated growth media at room temperature, and harvesting a cohesive filamentous biomat produced by the fungus. For biomats initiated from filamentous fungal spores, the method comprises inoculating a synthetic liquid growth media containing a carbon source with sterile spores, incubating the inoculated growth media at room temperature, and harvesting a cohesive filamentous biomat produced by the fungal spores.

In some embodiments, the fruiting body or spores of the filamentous fungus is selected from the group consisting of *Agaricus bisporus* (crimini and white), *Boletus edulis* (porcinini), *Cantarellus cibarius* (chantrelle), *Calvatia gigantea* (giant puffball), *Cyclocybe aegerita* (velvet piopinni), *Ganoderma lucidum* (Reishi), *Grifola frondosa* (maitake), *Morchella* species (Morel), *Hypsizygus tessellatus* (clamshell), *Hypsizygus ulmarius* (elm oyster), *Laetiporus* species (chicken of the woods), *Lentinula edodes* (shiitake), *Pleurotus eryngii* (trumpet royale), *Pleurotus ostreatus* (pearl oyster and blue oyster), *Pholiota microspora* (forest nameko), *Sparassis crispa* (cauliflower), and *Tuber* species (truffles). Sterile spores of the filamentous fungi were obtained from commercial venders, such as Myco Direct (Huntley, Ill.).

In still another embodiment, the filamentous biomat produced from planktonic cells, microconidia cells, sized reduced fruiting body, or spores of a filamentous fungus comprises less than 5 mm long aggregates of mycelia and/or hyphae. In yet another embodiment, the size reduced filamentous biomat comprises aggregates that are greater than 5 mm long.

In a further embodiment, the pH of the fruiting body cell inoculated growth media has a pH of about 4.0-4.1.

In another further embodiment, the carbon source for the synthetic growth media for fruiting body and/or cell growth comprises glycerol, starch, corn steep liquor, acid whey or combinations thereof and/or the incubation period is about 2-10 days or longer.

Another embodiment relates to a formulation of edible fungus filamentous biomat comprising edible fungal filamentous biomat particles isolated from the edible fungus filamentous biomats grown via surface fermentation on a synthetic liquid media.

Further embodiments relate to formulations that are in the form of a liquid, a solid or a gel.

Yet more embodiments relate to a formulation that is a paste, a flour, a porous/aerated mass and/or a firm mass.

Still another embodiment relates to a foodstuff comprising the formulation(s) of edible fungus filamentous biomat with or without other ingredients.

Additional embodiments are directed to foodstuffs made from the formulation(s) such as meat substitutes, drinks, beverages, yogurt, dessert, confections, or candy.

Another embodiment relates to a foodstuff made from the formulation(s) that is a mouse or a frozen dessert, such as an ice cream analogue, that does not melt at room temperatures.

Further embodiments relate to the use of the formulation(s) as an ingredient to augment and/or simulate the texture of a meat (e.g. a burger, sausage, hot dog, chicken or turkey nugget, and/or fish filet) in a foodstuff and/or to increase protein content of the foodstuff. Yet further embodiments relate to the use of liquid dispersion formulation(s) as a milk substitute and/or to increase the protein content of milk, milk products and/or milk substitute products.

Yet another embodiment relates to isolation of oils from an edible filamentous fungal biomat.

The present disclosure also provides a self-contained biofilm-biomat reactor. In one embodiment, the self-contained biofilm-biomat reactor comprises a container and placed within the container a feedstock, a fungal inoculum, a gas-permeable membrane(s), and optionally a liquid nutrient medium. In some embodiments the reactor is a one-time use reactor while in other embodiments the reactor can be reused.

Typically, the container in the various embodiments is capable of being sealed and may include a container cover in addition to a seal. In some embodiments the container is a covered tray. In other embodiments the container is a covered petrie dish or other type of covered container. In yet other embodiments, the container is a bag. In yet other embodiments, the container is a pipe with the upper portion made of a gas permeable membrane (2) (see FIG. 23). In some embodiments the container is comprised of a plurality of growth compartments. In some embodiments the container has a manifold design and/or a baffling system. In some embodiments the container is produced, either fully or partially, from one or more consumable feedstocks.

In some embodiments the feedstock is inoculated with an ascomycetes fungal strain, such as *Fusarium*, examples of which are *Fusarium oxysporum* strain MK7 (ATCC PTA-10698 deposited with the American Type Culture Collection, 1081 University Boulevard, Manassas, Va., USA), *Fusarium venenatum*, and *Fusarium avenaceum, Fusarium fujikuroi, Rhizopus* species, *Aspergillus* species, and/or combinations thereof.

In other embodiments the feedstock is inoculated with a basidiomycetes fungal strain, such as *Agaricus bisporus* (crimini and white), *Boletus edulis* (porcinini), *Cantarellus cibarius* (chantrelle), *Calvatia gigantea* (giant puffball), *Cyclocybe aegerita* (velvet piopinni), *Ganoderma lucidum* (Reishi), *Grifola frondosa* (maitake), *Morchella* species (Morel), *Hypsizygus tessellatus* (clamshell), *Hypsizygus ulmarius* (elm oyster), *Laetiporus* species (chicken of the woods), *Lentinula edodes* (shiitake), *Pleurotus eryngii* (trumpet royale), *Pleurotus ostreatus* (pearl oyster and blue oyster), *Pholiota microspora* (forest nameko), *Sparassis crispa* (cauliflower), and/or *Tuber* species (truffles).

In some embodiments the feedstock is a waste product, such as naturally occurring urine and/or feces, as well as food waste and by-products, industrial waste and/or by-products, agricultural waste and by-products, plant material, and/or combinations thereof. In other embodiments the feedstock can be a synthesized or manufactured surrogate, such as surrogate human urine. With respect to feedstock that is or includes plant material, that plant material is typically lignocellulosic. The lignocellulosic feedstock is selected from the group consisting of agricultural crop residues (e.g. wheat straw, barley straw, rice straw, pea, oat, small grain straw, corn stover, corn fibers (e.g. corn fiber gum (CFG), distillers dried grains (DDG), corn gluten meal (CGM), switch grass, hay-alfalfa, sugarcane bagasse, non-agricultural biomass (e.g. algal biomass, cyanobacterial biomass, urban tree residue), vegetables (e.g. carrots, broccoli, garlic, potato, beets, cauliflower), forest products and industry residues (e.g., softwood first/secondary mill residue, hard softwood first/secondary mill residue, recycled paper pulp sludge, anaerobic digestate), lignocellulosic containing waste (e.g. newsprint, waste paper, brewing grains, used rubber tire (URT), municipal organic waste, yard waste, clinical organic waste, sugar, starch, waste oils, olive oils, olive oil processing waste, cricket excrement, and waste generated during the production of biofuels (e.g. processed algal biomass, glycerol), and combinations thereof. Typically, the gas-permeable membrane is in direct contact with and sealed onto the surface of the one or more feedstock, optional liquid media, and inoculum present in the container. In some embodiments an optional culturing media is present.

In some embodiments the gas-permeable membrane is composed of a polymeric material, such as polypropylene, polyethylene, polytetrafluorethylene, polycarbonate, polyamide, polypyrrolone, poly(amidoamine) dendrimer composite, cellulose acetate, butadiene-acrylonitrile, TeflonAF2400, and nylon. In some embodiments the pore size for the gas-permeable membrane ranges from 0.05-1.5 μm, such as 0.2 μm, 0.45 μm, and 1.0 μm. In some embodiments the gas-permeable membrane is in the form of a sterile cloth-like material while in others the membrane is in the form of a paper-like material. In some embodiments the surface is smooth in texture, in others the surface is rough in texture. In some embodiments the path for gas diffusion is essentially direct while in others the path is tortuous.

In some embodiments the reactor produces a biofilm-biomat that serves as a food source, such as a protein source and/or an oil source. In other embodiments the biofilm-biomat serves as a leather analog and/or a bioplastic. In still other embodiments the biofilm-biomat serves as a source of biofuel precursors or as a biofuel itself. In yet other embodiments, the biofilm-biomat serves to produce organic products such as organic acids, antibiotics, enzymes, hormones, lipids, mycotoxins, vitamins, pigments and recombinant heterologous proteins.

DETAILED DESCRIPTION

Figure 1:
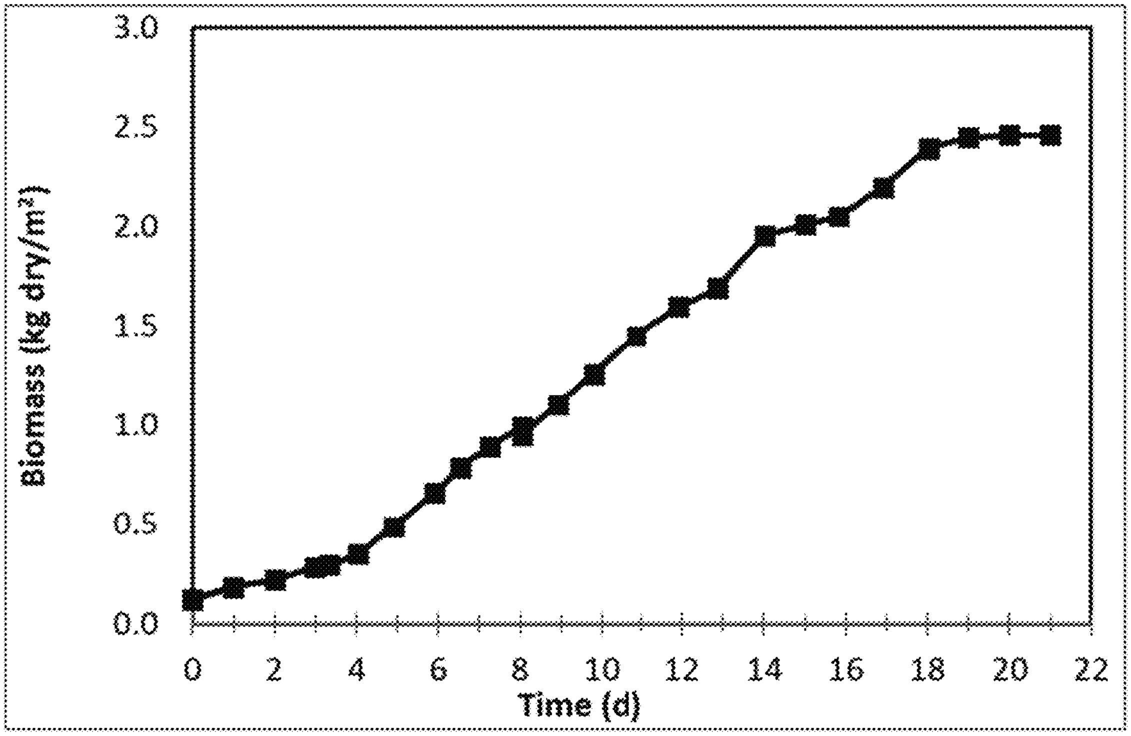
FIG. 1. Growth of *Fusarium oxysporum* strain MK7 biomat in nutrient medium that was refreshed daily after the initial 4-day biomat formation stage.

Edible filamentous fungi can be used as a protein source, either alone or incorporated into foodstuffs. For example, the protein content for pearl oyster mushrooms is 27.25%, for blue oyster mushrooms 24.65%, for reishi mushrooms 15.05% (Stamets (2005) Int J Medicinal Mushrooms 7:103-110), for giant puffballs 27.3% (Agrahar-Murugkar and Subbulakshmi (2005) Food Chem 89:599-603), and for cauliflower mushrooms 32.61% (Kimura (2013) BioMed Res. Int. Article ID 982317).

Yet while the fruiting bodies of Basidiomycota filamentous fungi, such as *Agaricus bisporus* (crimini and white), *Boletus edulis* (porcini), *Cantarellus cibarius* (chanterelle), *Ganoderma lucidum* (Reishi), *Morchella* species (Morel), *Hypsizygus tessellatus* (clamshell), *Pleurotus ostreatus* (pearl oyster and blue oyster), *Pleurotus eryngii* (trumpet royale), *Pholiota microspora* (forest nameko), *Sparassis crispa* (cauliflower), *Hypsizygus ulmarius* (elm oyster), *Cyclocybe aegerita* (velvet pioppini), *Grifola frondosa* (maitake), *Lentinula edodes* (shiitake), *Laetiporus* species (chicken of the woods), *Calvatia gigantea* (giant puffball), and *Tuber* species (truffles) are commonly used in foodstuffs, there are few products primarily comprising the vegetative mycelia of either the Basidiomycota or Ascomycota filamentous fungi. This is due, in part, to mycelia typically being either subterraneous or largely inseparable from the matter on which it grows.

Yet under particular conditions, filamentous fungi can form fungal biomats via surface fermentation under anaerobic, microaerobic, or aerobic conditions or a combination thereof. Here, the filamentous fungal biomats comprise the fungal species and/or strain and/or progeny thereof primarily in the form of mycelia, fragments of mycelia, hyphae, fragments of hyphae, and to a lesser extent contain conidia, microconidia, macroconidia, or any and all combinations thereof and in some cases can also contain pycnidia and chlamydospores.

Typically, the filamentous biomats are primarily comprised of mycelia; that is, a complex network of interwoven vegetative hyphae filaments. The average length of non-broken filaments within the biomat is generally at least 0.1 mm, such as between 0.1 mm-0.5 mm, 0.5 mm-50 cm, 0.6 mm-40 cm, 0.7 mm-30 cm, 0.8 mm-25 cm, 1.0 mm-20 cm, 1.4 mm-15 cm, 1.6 mm-10 cm, 1.7 mm-8 cm, 1.8 mm-6 cm, 2.5 mm-4 cm, and 5 mm-2 cm, 2 cm-25 cm, 4 cm-30 cm, 5 cm-40 cm, 6 cm-50 cm, 8 cm-60 cm, 10 cm-100 cm.

The growth of filamentous fungal biomats can be accomplished via surface fermentation. This involves inoculating liquid media containing a carbon source and a nitrogen source with filamentous fungal cells. Suitable carbon sources are sugars (e.g. sucrose, maltose, glucose, fructose, Japan rare sugars, etc.), sugar alcohols (e.g. glycerol, polyol, etc.), starch (e.g. corn starch, etc.), starch derivative (e.g. maltodextrin, cyclodextrin, glucose syrup, hydrolysates and modified starch), starch hydrolysates, hydrogenated starch hydrolysates (HSH; e.g. hydrogenated glucose syrups, maltitol syrups, sorbitol syrups, etc.), lignocellulosic pulp or feedstock (e.g. sugar beet pulp, agricultural pulp, lumber pulp, distiller dry grains, brewery waste, etc.), corn steep liquors, acid whey, sweet whey, milk serum, wheat steep liquors, carbohydrates, food waste, olive oil processing waste, hydrolysate from lignocellulosic materials, and/or combinations thereof. The filamentous fungal cells generate biomats which are located on the surface of the growth media; that is, they essentially float atop the growth media.

In many cases, especially for Ascomycota fungi, growth media was inoculated with an inoculum comprising planktonic filamentous fungal cells. High quality inoculum is composed of planktonic cells, which are defined as single cells that are not clumped or aggregated together, are preferably isolated from an exponential growth phase, and can include microconidia. Ideally, the cells of the inoculum float on the surface of the growth media, such as those cells having a high lipid content, and result in increased growth rate. Cells or clumps of cells that are submersed within the growth media negatively affect the cells floating on the surface and the biomats they form. Specifically, the biomats resulting from growth media containing a significant number of clumped submersed cells are typically discolored and tend to not grow homogeneously dense mats.

For Basidiomycota spore inoculation, approximately 2 cc of sterile spores suspended in deionized water from a spore syringe (e.g. MycoDirect, Huntley, Ill.) are used to inoculate approximately 75 mL of growth media in small Pyrex trays. Alternatively, 1 cc of spores suspended in deionized water from a spore syringe was plated on a container having malt extract agar media+CF (30 g dry malt extract, 20 g agar, 1000 mL water+0.01% chloramphenicol) using standard sterile conditions. Containers were sealed with parafilm and incubated at room temperature until mycelium completely covered the surface of the agar. A segment of mycelium from the agar preparation approximately 2 cm in width cut into a wedge was then diced into the smallest size possible before transferring to a tube with growth media. Liquid culture tubes were sealed, incubated at room temperature, and shaken by hand or shaken by mechanical means (i.e. continuous shaking or a continuous stirred tank reactor) for about 1 minute at least five (5) times per day to break up mycelium as much as possible. Liquid cultures were incubated until visually turbid, typically three or more days. The liquid cultures were then used to inoculate growth medium in trays at a 10% or 15% of total growth medium volume.

Basidiomycota fruiting bodies were also used to generate inoculum for initiating filamentous biomats. In some instances, inoculum was prepared by (a) surface sterilizing fruiting bodies, for example in a 5% bleach solution, (b) rinsing with sterile media, (c) grinding under sterile conditions to either less than 5 mm long aggregates or greater than 5 mm aggregates, depending on the final use, (d) surface sterilizing the ground mushroom biomass for example in a 5% bleach solution, and again rinsing with sterile media. 5 grams of the ground surface-sterilized fruiting body biomass was used directly as inoculum. In other instances, a pure culture derived from a fruiting body was used. Here, ~3 $mm^3$ portions of fruiting body was placed on agar media containing 0.01% chloramphenicol and incubated at room temperature. After 2-5 days of growth, hyphae were transferred onto fresh agar+chloramphenicol media and grown for another 3-7 days. Culture purity was confirmed by extracting and purifying DNA (FastDNA Spin Kit, MP Biomedicals), sequencing the 16S rRNA sequence and/or ITS region, and performing phylogenetic classification of the sequences using Blast (NCBI database). Upon confirmation, hyphae were used to inoculate 50 mL of sterile liquid media and agitated/rotated at 185 rpm for approximately 5 days before using as inoculum at a ratio of about 7.5% inoculum to 92.5% liquid media.

While a number of different media can be used, some media is not well adapted for growth of filamentous fungal biomats, such as Hansen's media (per liter=1.0 g peptone, 0.3 g $KH_2PO_4$. $7H_2O$, 2.0 g $MgSO_4$. $7H_2O$ 5.0 g glucose with a C:N ratio of 26.9) upon which full, cohesive biomats were not produced. Those media which work exceptionally well include MK7A, MK7-1, MK7-3 (all described in WO 2017/151684), as well as the media presented below.

Malt Medium 001 (C:N ratio of 19.1)

| Ingredient | Amount | Grade |
|---|---|---|
| Light Pilsner Malt | 40.0 g | Food |
| Peptone | 4.0 g | Research |
| Yeast Extract Powder | 1.2 g | Research |
| Canola Oil | 1.0 mL | Food |
| Ground Oats | 4.0 g | Food |
| Tap $H_2O$ | 1000 mL | N/A |

MK-7 SF Medium (C:N ratio of 7.5)

| Ingredient | Amount | Grade |
|---|---|---|
| $NH_4NO_3$ | 7.553 g | ACS |
| Urea | 2.548 g | USP |
| $CaCl_2$ | 2.000 g | Reagent |
| $MgSO_4$ * $7H_2O$ | 2.000 g | USP |
| $KH_2PO_4$ | 7.500 g | Reagent |
| Trace * | 2.000 mL | * |
| Glycerol | 0.075 Kg | Food/USP |
| Yeast Exract | 1.750 g | Research |
| $FeCL_2$ * $4H_2O$ | 0.020 g | Reagent |
| DI $H_2O$ | 0.940 L | N/A |

| Trace Components * | | |
|---|---|---|
| Micronutrients * | mg/L | Grade |
| FeSO4•7 H2O | 9.98 | ACS |
| ZnSO4•7 H2O | 4.4 | USP/FCC |
| MnCl2•4 H2O | 1.01 | Reagent |
| CoCl2•6 H2O | 0.32 | Reagent |
| CuSO4•5 H2O | 0.31 | Technical |
| (NH4)6Mo7O24•4H2O | 0.22 | ACS |
| H3BO3 | 0.23 | ACS |
| EDTA, free acid | 78.52 | Electrophoresis |

Malt Media 001 Supplemented with $NH_4NO_3$(C:N ratio of 7.5)

| Ingredient | Amount | Grade |
|---|---|---|
| $NH_4NO_3$ | 5.0 g | ACS |
| Light Pilsner Malt | 40.0 g | Food |
| Peptone | 4.0 g | Research |
| Yeast Extract Powder | 1.2 g | Research |
| Canola Oil | 1.0 mL | Food |
| Ground Oats | 4.0 g | Food |
| Tap $H_2O$ | 1000 mL | N/A |

Osmotic pressure readings were taken by sterilely removing 250 μl of media and using a recently calibrated Osmometer (Model 3250 SN: 17060594) capable of measuring up to 5000 mOsm. Three reading were taken and provided the following results: Hansen's=39, 39, 38; Malt 001=169, 168, 169; MK-7 SF=1389, 1386, 1387; Malt 001+$NH_4NO_3$=288, 287, 286.

In addition, the media used in our method can define the protein content of the resulting biomat. For example, while the natural protein content of the fruiting body of Blue Oyster mushrooms is reported to be 24.65% (Stamets (2005) Int J Medicinal Mushrooms 7:103-110) Blue Oyster biomats grown according to our method on Malt 001 media have a higher moisture corrected protein content of 29.82%, an increase in protein content of 5.71%. More strikingly, the protein content of fruiting bodies of Giant Puffball is reported to be 27.3% (Agrahar-Murugkar and Subbulakshmi (2005) Food Chem 89:599-603), yet Giant Puffball biomats grown with our method on Malt 001 media have a moisture corrected protein content of 32.04%, while MK7-1 SF media produces a moisture corrected protein content of 46.33% and Malt 001+$NH_4NO_3$ media produces a moisture corrected protein content of 46.88%, essentially an increase in protein content of 19.85% over that reported by Agrahar-Murugkar and Subbulakshmi.

Harvesting of biomats typically occurs after 2-3 days of growth, although in some instances longer growth periods are desirable, such as when thicker or denser biomats are desired/required. For example, growth periods of 3.5-4 days, 3-5 days, 4-6 days, 5-7 days, 6-9 days, 7-10 days, 19-21 days, or even up to 2 months may be desirable. Due to the cohesive structure of the filamentous biomats grown under surface fermentation conditions described in PCT/US2017/020050 and herein, the filamentous biomats have enough tensile strength to be lifted essentially intact from the surface of the media at the end of the growth period. Table 1 presents some examples tensile strength measured.

TABLE 1

Average Tensile Strength for some filamentous fungal biomats

| Organism | C source | Thickness (cm) | Width (cm) | Avg. Break wt (g) | Avg. Tensile Strength ($g/cm^2$) |
|---|---|---|---|---|---|
| Giant Puffball | Malt | 0.13 | 1.2 | 47.12 | 314.13 |
| | Glycerol | 0.10-1.3 | 1.2 | 29.05 | 214.85 |
| | MK7-1SF | 0.25-0.35 | 0.65-0.8 | 30.67 | 263.98 |
| | Malt + $NH_4NO_3$ | 0.09-0.10 | 0.9-1.1 | 27 | 281.15 |
| Cauliflower | Malt | 0.15-2.0 | 1.0-1.2 | 101.05 | 507.38 |
| | Glycerol | 0.09-0.20 | 1.2 | 202.17 | 242.91 |
| Reishi | Malt | 0.5 | 1.0-1.2 | 101.05 | 1854.54 |
| Blue Oyster | Malt | 0.5 | 1.2 | 43.40 | 72.74 |
| | Glycerol | 0.4 | 1.3 | 19.04 | 37.27 |
| Pearl Oyster | Malt | 0.5 | 1.0-1.2 | 56.7 | 98.96 |
| Elm Oyster | Malt | 0.35 | 1.2 | 50.28 | 143.67 |
| *F. oxysporum* strain MK7 | Glycerol | 0.5-0.8 | 1.0 | >742 | >570 |

Surface fermentation can be carried out under various conditions, including static media conditions (as described in PCT/US2017/020050), semi-static media conditions, and continuous media flow conditions.

Growth under semi-static media conditions means that at least a portion of the medium is replaced before the filamentous fungal biomat is harvested. These conditions allow linear dry biomass production from day 4 through day 18 ($r^2$=0.995), after which biomass weight stabilizes at about 2.5 Kg dry/$m^2$.

Biomats can also be produced under continuous media flow conditions where biomat growth is confined to the surface of the growth media where the medium underneath the mat is continuously refreshed or semi-continuously refreshed.

In some instances, however, it is desirable to harvest the growing biomat on a semi-continuous basis. Here, removal of some portion of the biomat occurs and the remaining portion is then physically moved to the open area of medium that was created by removal of the portion of biomat. This can be accomplished by physically grasping the biomat and pulling it until it touches the end of the surface fermentation container or by other mechanical means. The resulting open area is then available for new biomat growth without a separate or additional inoculation step since the medium already contains viable fungal cells. This process can be repeated periodically, which can be particularly useful when the medium is refreshed or nutrients that have become limited are reintroduced.

Biomat harvesting can also be done on a continuous basis. Continuous removal can be facilitated by a number of mechanisms. One such example is a roller wheel that is attached to the mature end of the biomat (see FIG. 7). The roller wheel slowly turns and harvests the mature biomat and at the same time creates open medium for growth of new biomat at the other end of the surface fermentation container. A typical rate of harvesting is 1.56 cm/day, although this can be altered for particular needs or as desired by a user.

Growth under membrane encapsulated/hermetically sealed bioreactor conditions involves encapsulating liquid growth medium with no gas headspace in an appropriate system/container. Appropriate systems/containers are, for example, trays, Petri dishes, or any container having a relatively large surface area to depth ratio. Gas permeable membranes are placed directly on the surface of the liquid medium and sealed tightly to the system/container. Appropriate membranes include, for example, polypropylene membranes (e.g. KC100 Kimguard, Kimberly-Clark, Roswell, Ga.), polyester membranes, polycarbonate membranes, silicone membranes, polyamide membranes, cellulose membranes, and ceramic membranes, to name but a few. Gas exchange between the growing biomats and the surrounding atmosphere occurs solely through the semi-permeable membrane.

In some cases, UVB light (290-320 nm) can trigger pigment production by filamentous fungi, such as for *Fusarium oxysporum* strain MK7, producing a pigmented biomat. In addition to a color change, which can be useful for creating various food effects, treatment with UVB converts ergosterol present in the fungal cell membranes into vitamin D2 and increases production of carotenoids, such as beta carotene and astaxanthin. Consequently, irradiating filamentous fungi, such as *Fusarium oxysporum* strain MK7, with UVB can be used to increase vitamin D2 and carotenoids in the resulting biomats.

In some cases, the filamentous fungal biomats formed are composed of layers of cells which are uniform in appearance, one surface of the filamentous biomat in contact with the air and one surface in contact with the synthetic media. In other cases, at least two distinct layers are present: an aerial hyphae layer at the top surface and a dense multicellular bottom layer in contact with the synthetic media. Oftentimes three distinct layers are present: (a) an aerial hyphae layer at the top surface, (b) a dense bottom layer and (c) a transitional layer between the top and bottom layers. The transitional layer may be only loosely attached to the dense bottom layer, in those cases enabling easy separation of the bottom layer from the rest of the biomat. Filament densities of the transitional layer range from slightly less dense than the bottom layer in the zone where the two layers meet, to a density that is comparable to the aerial hyphae near the top of the biomat.

Inactivation of Filamentous Fungal Biomats

The inactivation process begins with biornats harvested at least 2 days after cultivation. While biomats can be rinsed to remove excess growth media, biomat rinsing is not required, although in some cases the removal of growth media or excess growth media is preferable. Similarly, biomats can be squeezed to remove excess growth media, again not required, but which may be preferable for some applications.

Elimination of cell viability and the potential of further biomat growth is desired in some instances, such as for use of the biomat as a stand-alone protein source or a protein ingredient in foodstuffs. This can be accomplished by heating, irradiation, and/or steaming.

For the heating process, filamentous fungal biomats can be treated according to WO 95/23843 or British Patent No 1,440,642, for example, or incubated at temperatures that destroy the vast majority of the organism's RNA without adversely affecting the organism's protein composition.

In irradiation, filamentous fungal biomats are exposed to ionizing energy, such as that produced by $^{60}$Co (or infrequently by $^{137}$Cs) radioisotopes, X-rays generated by machines operated below a nominal energy of 5 MeV, and accelerated electrons generated by machines operated below a nominal energy of 10 MeV.

Steaming is the preferred method for inactivating some filamentous fungal biomats, such as those produced by *Fusarium oxysporum* strain MK7 and *F. venentatum*, as steaming can also remove some specific metabolites from the biomat construct if those metabolites are produced. Here, biomats are placed such that biomat excreted liquids and condensed steam can easily drip away from the biomats. Suitable biomat holding systems include porous plastic mesh and porous trays. Other biomat holding systems include, but are not limited to, systems that secure the biomat in a vertical position, such as systems with a clamping mechanism that clamps at least one end of a biomat while the remaining end(s) of the biomat hang from said clamp and mesh systems which clamp at least two sides of the biomat, to name but a few.

Biomats are positioned within a steamer such that heated steam, such as steam of a temperature greater than 85° C., for example 95° C., comes into contact with the biomats. In those cases where multiple trays are placed in a single steamer, for example one tray above the other, it is preferred to protect a lower positioned biomat from the drippings of a higher positioned biomat. Protection should be of a form which allows steam to contact biomats, thereby de-activating biomat viability, and to also deflect biomat excreted liquids and condensed steam produced at a higher level in the steamer from contacting biomats positioned at a lower level in the steamer. In one embodiment, a cone is positioned between an upper tray and a lower tray to accomplish this result. In other embodiments, separation between upper and lower trays also include at least one other geometric shape such as a cylinder, a cube and/or cuboid, a pyramid, a sphere, a tori, and/or other platonic solids. In yet another embodiment, trays are separated using at least one cylinder, cube and/or cuboid, pyramid, sphere, tori, other platonic solid, or combinations thereof.

Biomats are steamed at least to the point where biomat viability is reduced such that further biomat growth and/or cellular reproduction within a biomat is negligible. Biomat viability is a function of the original substrate, biomat development, steam/heat transfer characteristics, biomat position in a steamer and biomat orientation relative to evolved steam. As an example, *Fusarium oxysporum* strain MK7 biomats grown on a glycerol or acid whey substrate are non-viable after 5 minutes, and in some cases less than 5 minutes, of steaming. Steamed mats can be rinsed and/or squeezed to remove mat excretions and condensed steam.

The inactivated edible filamentous fungal biomats can be used directly as a protein source, for example in preparing foodstuffs largely comparable to tofu, bacon, and jerky, to name but a few.

The inactivated edible filamentous fungal biomats can also be size reduced for use as a protein source in foodstuffs. The size reduction can occur by mechanical means such as cutting, chopping, dicing, mincing, grinding, blending, etc. or via sonication and is conducted prior to mixing with other ingredients or liquids. Size reduced particles can be uniform in size or variable. Typically, the length of the sized reduced particles is between 0.05-500 mm, the width is between 0.03-7 mm, and height is between 0.03-1.0 mm. For example, flour-type particles typically range between 0.03 mm and 0.4 mm, jerky-type particles range between 100 mm and 500, etc. Larger size particles can be produced, biomats have been grown in inflatable pools (66" in diameter) producing a single biomat 66" in diameter and completely round. Larger vessels can be used to grow even larger mats.

The number of size reduced particles produced per biomat is dependent on the initial biomat size and the purpose for which the biomat size reduced particles will be used.

Depending on the foodstuff, the size reduced particles contain average unbroken filament lengths of at least 0.1 mm, such as between 0.1 mm-2.0 mm, 0.5 mm-10 cm, 0.5 mm-30 cm, 0.8 mm-25 cm, 1.0 mm-20 cm, 1.4 mm-15 cm, 1.6 mm-10 cm, 1.7 mm-8 cm, 1.8 mm-6 cm, 2.5 mm-4 cm, 5 mm-2 cm, 0.5-2.5 mm, 0.5-1.8 mm, 0.5-1.7 mm, 0.5-1.6 mm, 0.5-1.4 mm, 0.5-1.0 mm, 0.5-0.8 mm, 0.5-0.6 mm, 0.6-2.5 mm, 0.6-1.8 mm, 0.6-1.7 mm, 0.6-1.6 mm, 0.6-1.4 mm, 0.6-1.0 mm, 0.6-0.8 mm, 0.8-2.5 mm, 0.8-1.8 mm, 0.8-1.7 mm, 0.8-1.6 mm, 0.8-1.4 mm, 0.8-1.0 mm, 1.0-2.5 mm, 1.0-1.8 mm, 1.0-1.7 mm, 1.0-1.6 mm, 1.0-1.4 mm, 1.4-2.5 mm, 1.4-1.8 mm, 1.4-1.7 mm, 1.4-1.6 mm, 1.6-2.5 mm, 1.6-1.8 mm, 1.6-1.7 mm, 1.7-2.5 mm, 1.7-1.8 mm, or 1.8-2.5 mm, as well as larger size distributions such as between 0.1-1.0 cm, 0.5-2.0 cm, 1.0-5.0 cm, 2.0-7.0 cm, 5.0-10.0 cm, 7.0-20 cm, 10.0-50.0 cm, and 15.0-100.0 cm.

Size reduced particles of the filamentous fungal biomats also contain broken filaments and, in some cases, broken filaments are primarily present, such as 100% broken filaments, 99% broken filaments, 98% broken filaments, 97% broken filaments, 96% broken filaments, and 95% broken filaments. Again, the size of the broken filaments is selected for the ultimate foodstuff produced. Average broken filament lengths can range from at least 0.01 mm, such as between 0.01-0.10 mm, 0.05-0.20 mm, 0.1-1.0 mm, 0.50-2.5 mm, 1.0-5.0 mm, 2.0-10.0 mm, 5.0 mm-15.0 mm, 10.0 mm-1.0 cm, 1.0 cm-5.0 cm, 5.0 cm-10.0 cm, 0.3 mm-30 cm, 0.8 mm-25 cm, 1.0 mm-20 cm, 1.4 mm-15 cm, 1.6 mm-10 cm, 1.7 mm-8 cm, 1.8 mm-6 cm, 2.5 mm-4 cm, 5 mm-2 cm, 0.3-2.0 mm, 0.3-1.8 mm, 0.3-1.7 mm, 0.3-1.6 mm, 0.3-1.4 mm, 0.3-1.0 mm, 0.3-0.8 mm, 0.3-0.6 mm, 0.3-0.5 mm, 0.6-2.5 mm, 0.6-1.8 mm, 0.6-1.7 mm, 0.6-1.6 mm, 0.6-1.4 mm, 0.6-1.0 mm, 0.6-0.8 mm, 0.8-2.5 mm, 0.8-1.8 mm, 0.8-1.7 mm, 0.8-1.6 mm, 0.8-1.4 mm, 0.8-1.0 mm, 1.0-2.5 mm, 1.0-1.8 mm, 1.0-1.7 mm, 1.0-1.6 mm, 1.0-1.4 mm, 1.4-2.5 mm, 1.4-1.8 mm, 1.4-1.7 mm, 1.4-1.6 mm, 1.6-2.5 mm, 1.6-1.8 mm, 1.6-1.7 mm, 1.7-2.5 mm, 1.7-1.8 mm, or 1.8-2.5 mm.

In some cases, the average broken filament length in the reduced particles of the filamentous fungal biomats is less than 1 um, such as less than 950 nm, less than 900 nm, less than 850 nm, less than 800 nm, less than 750 nm, less than 700 nm, less than 650 nm, less than 600 nm, less than 550 nm, less than 500 nm, or less than 400 nm.

The reduced particle size of the filamentous fungal biomat can be added as a protein source to augment the protein content of a foodstuff or can be the sole protein component. For foods composed entirely of filamentous fungal biomats, the size reduced particles can be optimized for particular textures, mouth feel, and chewiness. For example, a filamentous fungal biomat food shaped and seasoned to resemble a hamburger can have 90% of the particles with lengths less than 1.5 mm and the majority of lengths being 1 mm or less, widths of less than 1 mm, and depths of less than 0.75 mm. This type of food is characterized as having a higher perceived density in the mouth, is easier to chew, offers a creamy mouth feel and a more refined food experience. Highly processed biomat particles have been compared to the type of burger found in fine dining establishments. For a more heartier food experience similar to the type of burger prepared commonly found in burger restaurants or BBQ's, 90% of the particles have lengths between 4 mm and 10 mm, widths of 1.0 mm to 3 mm, and depths of less than 0.75 mm. The ability to alter texture, mouth feel, and chewiness allow customization to accommodate individuals having particular dietary needs, such as those that have trouble chewing, or who require/desire softer foods while still providing the same nutritional and taste experience or those who desired food with more texture, more mouthfeel and more mastication. Because of the ability to easily control the particle size, foods augmented with filamentous fungal biomats or made solely from filamentous fungal biomats have textures very similar to the standard protein foods that they emulate, as can be seen in Table 2.

TABLE 2

Results from Stable Micro Systems TA XT plus texture analyzer

| Food | Avg. Max Hardness | Avg. Area (g/mm) | Avg. Mean (g) | Parameters |
|---|---|---|---|---|
| Fish Stick | | | | |
| Commercial fish stick | 3654 ± 1774 | 17868 ± 5674 | 894 ± 284 | Pre-Test Speed: 2.00 mm/sec<br>Test Speed: 4.00 mm/sec |
| MK7 fish stick | 1618 ± 180 | 19990 ± 610 | 1000 ± 100 | Post-Test Speed: 10.00 mm/sec |
| Chicken Nugget | | | | |
| Commercial chicken nugget | 3838 ± 56.8 | 27329 ± 3663 | 1367 ± 183 | |
| Quorn chicken nugget | 4013 ± 1066.3 | 27751 ± 1346.4 | 1415 ± 111.4 | Target Mode: Distance<br>Force: 100.0 g |
| MK7 small particle | 3127 ± 19.7 | 33065 ± 3458 | 1654 ± 173 | Distance: 20.000 mm<br>Strain: 10.0% |
| MK7 medium particle | 2514 ± 663 | 27217 ± 6437 | 1361 ± 322 | Trigger Type: Auto (Force)<br>Tigger Force: 5.0 g |
| MK7 large particle | 3461 ± 77.8 | 34591 ± 2971.2 | 1730 ± 14.6 | Probe: HDP/WBV<br>Warner Bratzler V Slot Blade |
| Burger | | | | |
| 100% Beef burger | 4326 ± 714 | 12350 ± 46.1 | 1727 ± 14.1 | |
| 90% Beef, 10% MK7 | 5011 | 14048 | 1929 | |
| 80% Beef, 20% MK7 | 2615 ± 199 | 10641 ± 511 | 1456 ± 46 | |
| 70% Beef, 30% MK7 | 2240 ± 262 | 9859 ± 2947 | 1291 ± 300 | |
| 60% Beef, 40% MK7 | 2094 ± 156 | 8118 ± 1088 | 1155 ± 180 | |
| 100% MK7, chopped (highly processed) | 2228 ± 1988 | 5079 ± 964 | 1089 ± 70.6 | |

TABLE 2-continued

| Results from Stable Micro Systems TA XT plus texture analyzer | | |
|---|---|---|
| Food | Firmness (g) | |
| Chocolate Mousse | | |
| Nestle chocolate mousse | 182.45 | Pre-Test Speed: 1.00 mm/sec<br>Test Speed: 1.00 mm/sec<br>Post-Test Speed: 10.00 mm/sec |
| MK7 chocolate mousse | 135.09 | Target Mode: Distance<br>T.A. Variable No: 5: 0.0 g<br>Distance: 10.000 mm<br>Strain: 10.0%<br>Trigger Type: Auto (Force)<br>Tigger Force: 5.0 g<br>Probe: P/25; 25 mm DIA<br>Cylinder Aluminum |

Examples of foods that can be produced using only the reduced particle size of the filamentous fungal biomat, with or without added flavorings, and/or that can be augmented with the reduced particle size of the biomat are meat products (such as ground beef, ground chicken, ground turkey, chicken nuggets, fish sticks or patties, jerky, snacks (e.g. chips), soups, smoothies, beverages, milk analogues, breads, pastas, noodles, dumplings, pastries (e.g. Pate a Choux), cookies, cakes, pies, desserts, frozen desserts, ice cream analogues, yogurt, confections, and candy.

Foods augmented with the reduced particle size of the filamentous fungal biomat can significantly increase the protein content, which is particularly important for individuals following a vegan diet. For example, augmenting a cup of soup (227 g) with 68.1 g of MK7 liquid dispersion (i.e. 1 part MK7 to 3 parts water) adds 8.5 g of protein and augmenting a bowl of soup (340 g) with 136 g of MK7 liquid dispersion adds 17 g of protein. Use of MK7 liquid dispersion as the primary ingredient, such as in vegan soups, drinks, smoothies, etc. further increases the protein content of these foods. Changing the MK7 to water ratio will in turn change the degree of protein augmentation.

Whether the reduced particle size of the biomat is used to augment the protein content of food or is used as the sole protein component, in some instances binders are helpful in achieving the desired texture. Approved foodstuff binders are envisaged, such as egg albumen, gluten, chickpea flour, vegetarian binders, arrowroot, gelatin, pectin, guar gum, carrageenan, xanthan gum, whey, chick pea water, ground flax seeds, egg replacer, flour, Chia seeds, psyllium, etc which can be used singularly or in combination. In addition to foodstuff binders, the reduced particle size of the filamentous fungal biomat can also be mixed with approved flavors, spices, flavor enhancers, fats, fat replacers, preservatives, sweeteners, color additives, nutrients, emulsifiers, stabilizers, thickeners, pH control agents, acidulants, leavening agents, anti-caking agents, humectants, yeast nutrients, dough strengtheners, dough conditioners, firming agents, enzyme preparations, gasses, and combinations thereof. Typically, binders, flavors, spices, etc. are selected to meet the demands of a particular population. For example, milk and/or milk solids are not used to accommodate individuals with dairy allergies/sensitivities, wheat flour may not be used to accommodate those with gluten allergies/sensitivities, etc.

In some applications, the reduced particle size filamentous fungal biomat is used in foodstuffs that simulate, chicken nuggets, turkey, pork, fish, burgers, sausages, jerky, bacon, and the like. Here, a single type of reduced particle size filamentous fungal biomat can be used or a variety of reduced particle sizes. Similarly, the reduced particle sizes can be from a single source of filamentous fungal biomat or from a combination of different sources of filamentous fungal biomats; e.g. MK7 alone or MK7+Giant Puffball biomats.

In some applications, the reduced particle size filamentous fungal biomat is dried, ground to a sufficiently small particle size and used as a flour for production of augmented protein baked goods, such as bread, rolls, muffins, cakes, cookies, pies, etc.

One aspect of introducing protein into a foodstuff is to use a liquid dispersion, made from the filamentous fungal biomat as a replacement ingredient for milk or a milk analogue. The liquid dispersion can be used in a number of recipes including soups, ice cream, yogurt, smoothies, fudge, and candies such as caramel and truffles. In some cases, the filamentous fungal biomats produced from different feedstocks/carbon sources result in liquid dispersions having different flavors. For example, when the feedstock/carbon source is glycerol, the resulting liquid dispersion produced from *Fusarium oxysporum* strain MK7 is sweeter while a liquid dispersion resulting from *Fusarium oxysporum* strain MK7 grown on an acid whey feedstock/carbon source tends to be sourer. The native sweetness or sourness of the filamentous fungus, e.g. *Fusarium oxysporum* strain MK7, transfers to the ultimate food product. For instance, acid whey liquid dispersions lends itself to yogurt, while glycerol liquid dispersions tends to lend itself to mouse, caramel or fudge.

The filamentous fungal biomat:water ratio can be adjusted to produce a liquid dispersion of the appropriate consistency and density. Ratios can be from 1:2 to 10:1, with preferred ratios as 1:3, 1:4, and 7:3. For example, a relative density ratio of 1:3 is amenable to ice cream analogues, beverages and yogurt.

In some cases, the filamentous fungal biomat can be used as a source of oil, for example truffle oil produced from surface fermentation edible fungal biomats of *Tuber* species.

The use of filamentous fungi as valuable microbial factories has been exploited in the past, but has generally required significant infrastructure and/or equipment, energy requirements, expensive reagents, and/or significant human resources. Filamentous fungi are well known for having the greatest metabolic diversity of all microorganisms on Earth, including the ability to produce a wide spectrum of organic adds, antibiotics, enzymes, hormones, lipids, mycotoxins, vitamins, organic acids, pigments, and recombinant heterologous proteins (Wiebi (2002) Myco-protein from

*Fusarium venenatum*: a well-established product for human consumption. Appl Microbiol Biotechnol 58, 421-427; El-Enshasy (2007) Chapter 9-Filamentous Fungal Cultures—Process Characteristics, Products, and Applications. In. Bioprocessing for Value-Added Products from Renewable Resources. Editor: Shang-Tian Yang. Elsevier; Gibbs et al (2000) Growth of filamentous fungi in submerged culture: problems and possible solutions. Crit. Rev. Biotechnol. 20, 17-48), as well as the ability to degrade many types of recalcitrant materials such as lignocellulose and humic substances in soils.

While widely used, significant challenges to production by submerged fermentation still exist and include important factors such as growth limitation due to the restricted oxygen availability and excessive shear forces generated by agitation (Gibbs et al (2000) Growth of filamentous fungi in submerged culture: problems and possible solutions. Crit. Rev. Biotechnol. 20, 17-48). Since oxygen solubility in water under Earth surface conditions is about 8 mg/L, it is readily depleted during rapid growth in submerged cultures. Thus, continuous aeration using complex, expensive and energy intensive aeration and agitation systems is required to maintain high growth rates. The cultivation of filamentous fungi is even more challenging since the filamentous morphology imparts non-Newtonian rheologicM behavior that further inhibits oxygen transfer to solution (Norregaard et al. (2014) Filamentous Fungi Fermentation. In Industrial Scale Suspension Culture of Living Cells, H.-P. Meyer, and D. R. Schmidhalter, eds. (Wiley-VCH Verlag GmbH & Co. KGaA), pp. 130-162). As culture densities increase, the amount of energy required to aerate and mix the cultures increases nonlinearly as well as the energy requirements to aerate dense cultures are very high. For many filamentous species, vigorous agitation and aeration of the cultures becomes detrimental to hyphal growth and as a result dramatically decreases growth rate. These and other challenges to submerged fermentation of filamentous microorganisms require innovative solutions to effectively harness these organisms with the limited resources available in spacecraft and at extraterrestrial stations.

The disclosed hermetic reactor system (1) addresses these problems and has the following advantages:

- Active aeration or agitation of the liquid culture is not necessary
- In-situ aggregation of biomass into a single coherent mat with significant tensile strength (>0.1 kg/cm of biomat width) allows easy harvesting
- Textured biomats can be used for a wide variety of mission critical products (i.e. food, bioplastics, biofuels, nutritional supplements, and as an expression platform for a variety of pharmaceuticals
- Minimal water use as well as minimal and/or no residual waste water or nutrients from the process while maintaining high biomass production (80-120 g/$m^2$/d or 0.55 g/L/h)
- Growth rates can translate to the production of fully formed biomats in as little as 2 days or can be further expanded for more than 10 days
- High biomass density (biomats are typically 100-180 g/L)
- A variety of filamentous fungi (including extremophiles) with specific advantages for different processes can be grown
- Scale-up or down is relatively straightforward and does not result in decreased producti vi ty.
- Process can use a very wide variety of C and N-rich waste substrates that arise from natural disasters and/or space missions.

The disclosed hermetic reactor system (1) provides a self-contained biofilm-biomat reactor comprising a container and placed within the container a feedstock, a fungal inoculum, a gas-permeable membrane (2), and optionally a liquid nutrient medium. Depending upon the circumstances, the reactor can be a one-time use reactor or a reusable reactor.

Typically, the container is capable of being sealed and may include a container cover in addition to a seal. Some container examples are a covered tray, a covered petrie dish, another type of covered container, or a bag. For some uses or in some environments the container has a plurality of growth chambers, for example following a manifold design and/or a baffling system. To maximize efficiency in some environmental conditions, the container is produced from one or more feedstocks; these may or may not be identical to the feedstock placed within the container.

The feedstock is inoculated with a fungal strain, such as an ascomycetes or basidiomycetes fungal strain. Examples of ascomycetes strains are *Fusarium oxysporum* strain MK7 (ATCC PTA-10698 deposited with the American Type Culture Collection, 1081 University Boulevard, Manassas, Va., USA), *Fusarium venenatum, Fusarium avenaceum*, and/or combinations thereof. Inoculation of the feedstock can occur at the time the feedstock is placed within the container or can occur sometime after the feedstock has been placed. That is, the hermetic reactor (1) can be primed with freeze-dried filamentous fungal inoculum that is revived upon contact with the feedstock or the feedstock can be directly inoculated after placement in the hermetic reactor channel(s) (4) or the feedstock can be inoculated and then placed in the hermetic reactor channel(s).

With respect to the feedstock used in the reactor, the feedstock can be a waste product, such as naturally occurring urine and/or feces, food waste, plant material, industrial waste such as glycerol, and waste by-products, starch and/or by products of starch hydrolysis, acid whey, sugar alcohol, and/or combinations thereof. Synthesized or manufactured waste surrogates, such as surrogate human urine can also be used. Plant material feedstocks are typically lignocellulosic. Some examples of lignocellulosic feedstock are agricultural crop residues (e.g. wheat straw, barley straw, rice straw, small grain straw, corn stover, corn fibers (e.g. corn fiber gum (CFG), distillers dried grains (DDG), corn gluten mean (CGM), switch grass, sugar beet pulp, waste streams from palm oil production, hay-alfalfa, sugarcane bagasse, non-agricultural biomass (e.g. algal biomass, cyanobacterial biomass, urban tree residue), forest products and industry residues (e.g., softwood first/secondary mill residue, hard softwood first/secondary mill residue, recycled pater pulp sludge), lignocellulosic containing waste (e.g. newsprint, waste paper, brewing grains, used rubber tire (URT), municipal organic waste and by-products, yard waste and by-products, clinical organic waste and by-products, and waste and by-products generated during the production of biofuels (e.g. processed algal biomass, glycerol), and combinations thereof.

A gas-permeable membrane(s) (2) allows optimization of the system in several different ways that are illustrated in FIGS. 19-22. While the hermetic reactor system illustrated in the Figures has a total of nine channels (4), the skilled artisan appreciates that any number of channels (4) can be present, from a single channel (4) to a plethora of channels (4), depending on the space available for placement the hermetic reactor (1). Similarly, the shape of the channels (4)

is not limited to a rectangular prisms or cylinders and can take any shape suitable to fit the available for the hermetic reactor (1).

Figure 16:
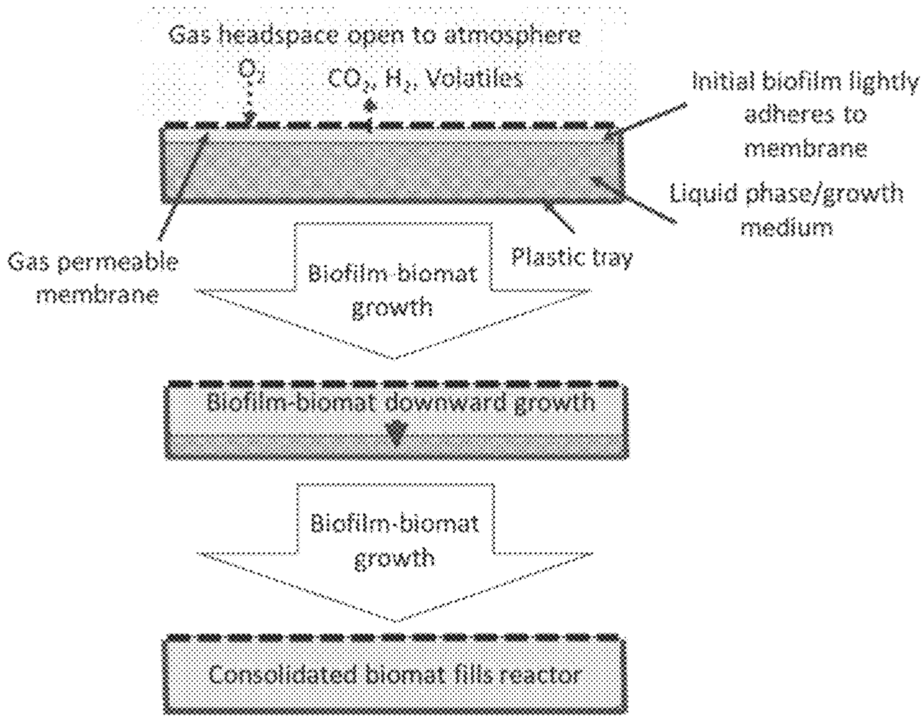
FIG. 16. Formation of biofilm-biomat in the encapsulated reactor starts when cells attach to the gas-permeable membrane where oxygen is readily available. Over time, biofilm-biomat grows downward and ultimately fills the space of the reactor, consuming all liquid and nutrients.

In some cases, the membrane (2) is placed in direct contact with the surface of the feedstock, optional liquid media, and inoculum present in the container as shown in FIG. 16. The membrane can also be sealed in contact with the surface of the feedstock, for example, by attaching it to a plastic frame with an integrated rubber gasket.

Figure 19:
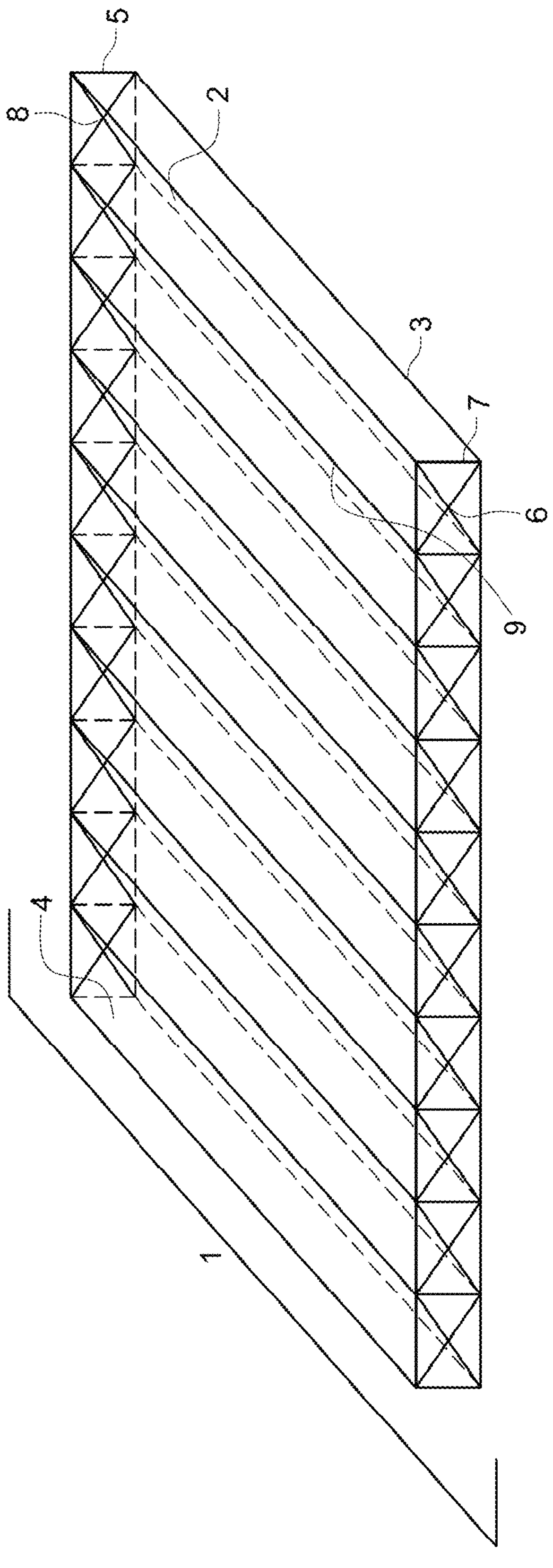
FIG. 19. Basic hermetic reactor (1). Multiple channels (4) with shared walls/baffles (9), front valves (6) and back valves (8) and a gas permeable membrane (2) are shown.
Figure 20:
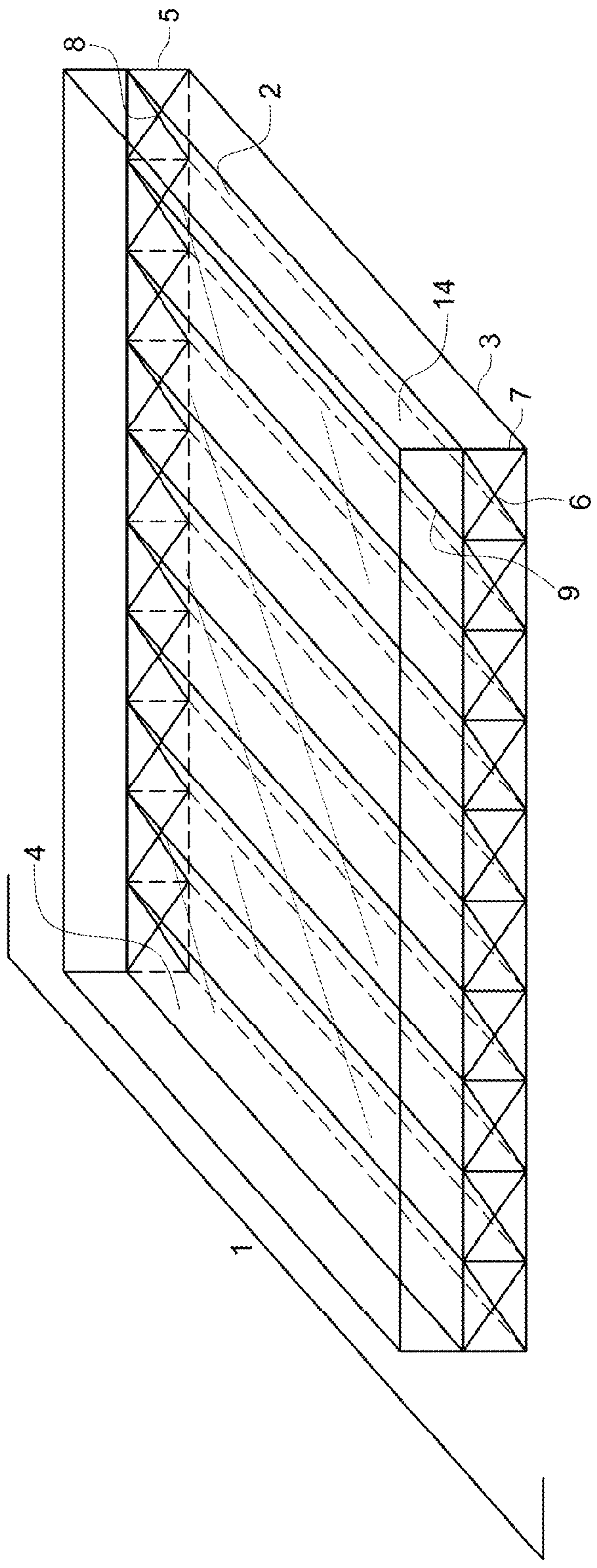
FIG. 20. Basic hermetic reactor (1) with a single gas collection chamber (14).
Figure 21:
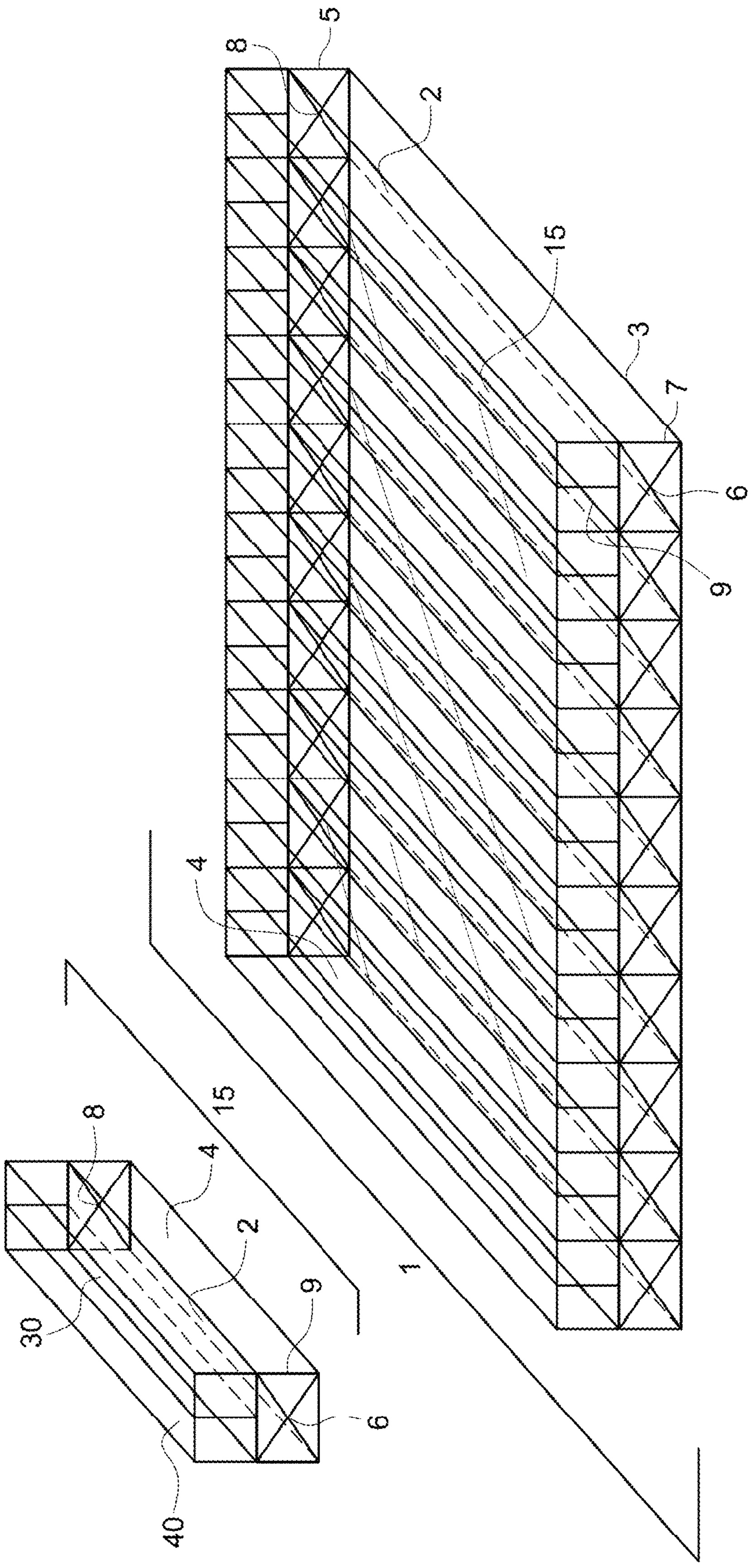
FIG. 21. Basic hermetic reactor (1) with channeled gas collection chambers (15) having gas specific channels (30, 40).

In other instances, the membrane is suspended over the feedstock so that as the fungi grows and consumes oxygen, the membrane drops down towards the mat or onto a baffle system located between the membrane and the feedstock which allow for growth of aerial hyphae. Such as system is shown in FIG. 19. Here, the hermetic reactor (1) is comprised of multiple channels (4) which initiate at an inlet valve (6) at the front (7) of the reactor, terminate at an outlet valve (8) at the back (5) of the reactor, and are separated by baffles/walls (9). A gas permeable membrane (2) forms the top of the reactor. The bottom (3) of the reactor can be formed of any suitable substance including, but not limited to both hard and soft plastics such as polyethylene terephthalate, high density polyethylene, polyvinyl chloride, polyactic acid, polycarbonate, acrylic, acetal, nylon, acrylonitrile butadiene styrene, glass, metals such as aluminum, titanium, stainless steel etc. and/or combinations thereof. The baffles/walls (9) can be made of similar materials. Suitable front (6) and back (8) valves include, but are not limited to, one-way valves, 2-way valves, ball valves, butterfly valves, gate valves, plug valves, globe valves, pinch valves, disc check valves, attached valves, detached valves, and/or combinations thereof. The inlet valve (6) serves to provide access to the chamber (4) for delivery of feedstock/media to the chamber while the outlet valve (8) allows removal of exhausted feedstock and/or filamentous fungal biomat. The gas-permeable membrane (2) can be composed of a polymeric material, such as polypropylene, polyethylene, polytetrafluorethylene, polycarbonate, polyamide, polypyrrolones, poly(arnidoarnine) dendrimer composite, cellulose acetate, butadiene-acrylonitrile, TeflonAF2400, and nylon. While the pore size of the gas-permeable membrane (2) typically ranges from 0.05-1.5 μm, such as 0.2 μm, 0.45 μm, and 1.0 μm, the membrane (2) can be in the form of a sterile cloth-like material or the form of a paper-like material. For some uses, the membrane's surface is smooth in texture, for others the surface is rough in texture. In addition, the path for gas diffusion can vary from being essentially direct to following a more tortuous path.

Figure 18:
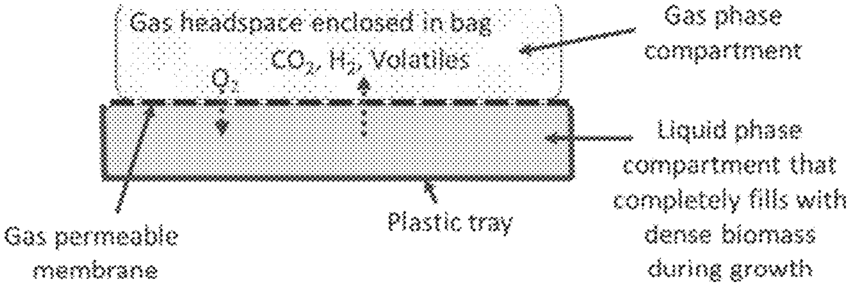
FIG. 18. An attached bag separated from the liquid medium by a gas-permeable membrane is used to supply and capture gasses. The integrated multi-functional membrane allows for ingress of oxygen and egress of $CO_2$ and other produced gases. Fungal biomass grown in the lower liquid compartment (yellow) converts the feedstocks and nutrients into biomat that fills the compartment as it grows. The dense consolidated biomat can be easily harvested by opening the reactor closure system (e.g. Zip-Lock® type) and removal from the bag.

In other situations, the membrane facilitates ingress of oxygen and egress of other gases produced during fungal growth (FIG. 18). In this situation the hermetic reactor (1) has a gas collection chamber (14) that is immediately atop of the gas permeable membrane (2) (see FIG. 20). The gas collection chamber (14) can be made of similar materials to those used for the walls/baffles (9) or the bottom (3) of the reactor; i.e. both hard and soft plastics such as polyethylene terephthalate, high density polyethylene, polyvinyl chloride, polyactic acid, polycarbonate, acrylic, acetal, nylon, acrylonitrile butadiene styrene, glass, metals such as aluminum, titanium, stainless steel etc. and/or combinations thereof. Alternatively, the gas collection chamber is comprised of channels (15) which can mirror the channels (4) of the hermetic reactor (1) or which encompass more than one of the hermetic reactor channels (4) (see FIG. 21).

Figure 22:
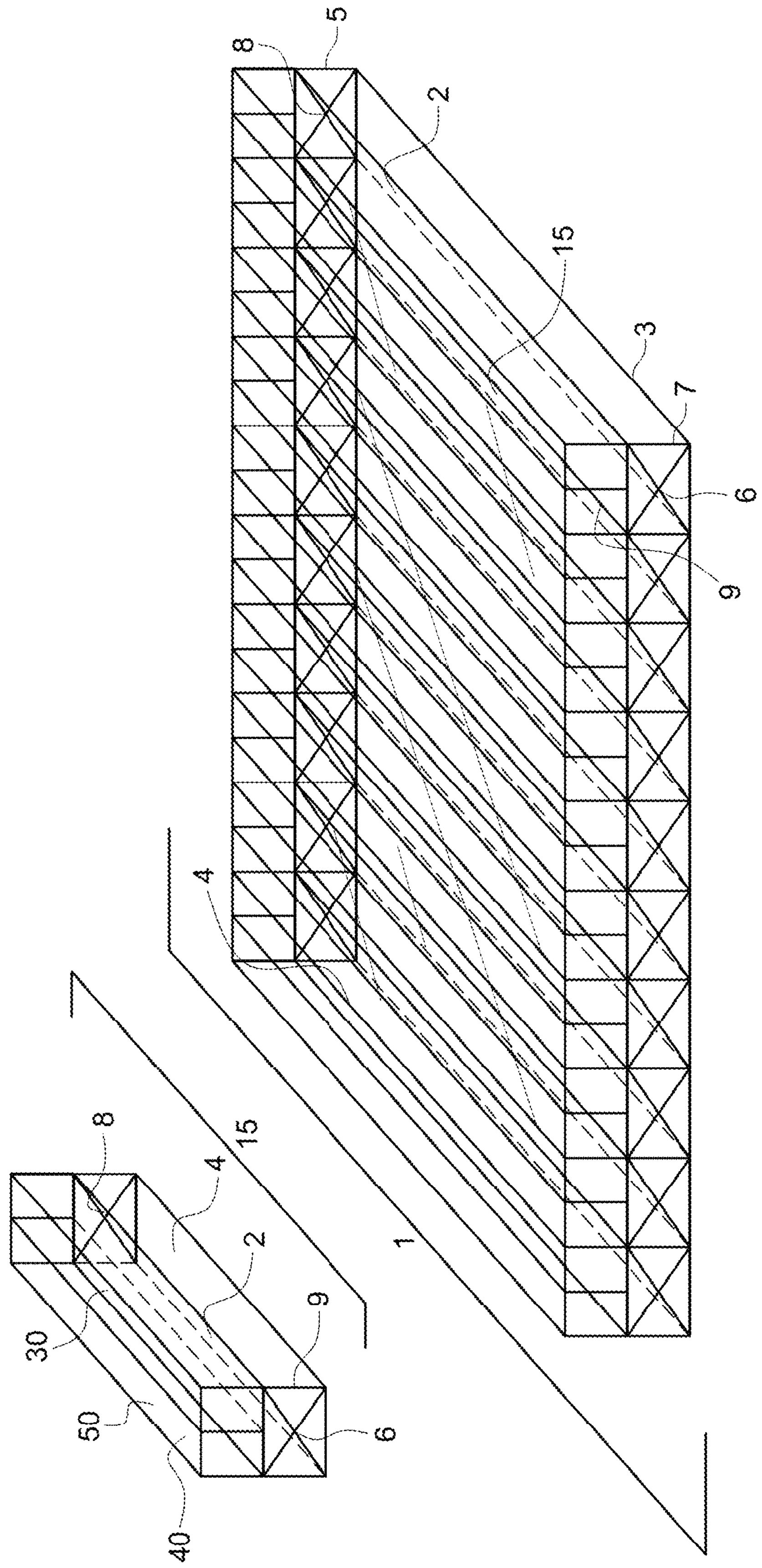
FIG. 22. Basic hermetic reactor (1) with channeled gas collection chambers (15) having gas specific channels (30, 40) with gas specific permeable membranes (2, 50).
Figure 23:
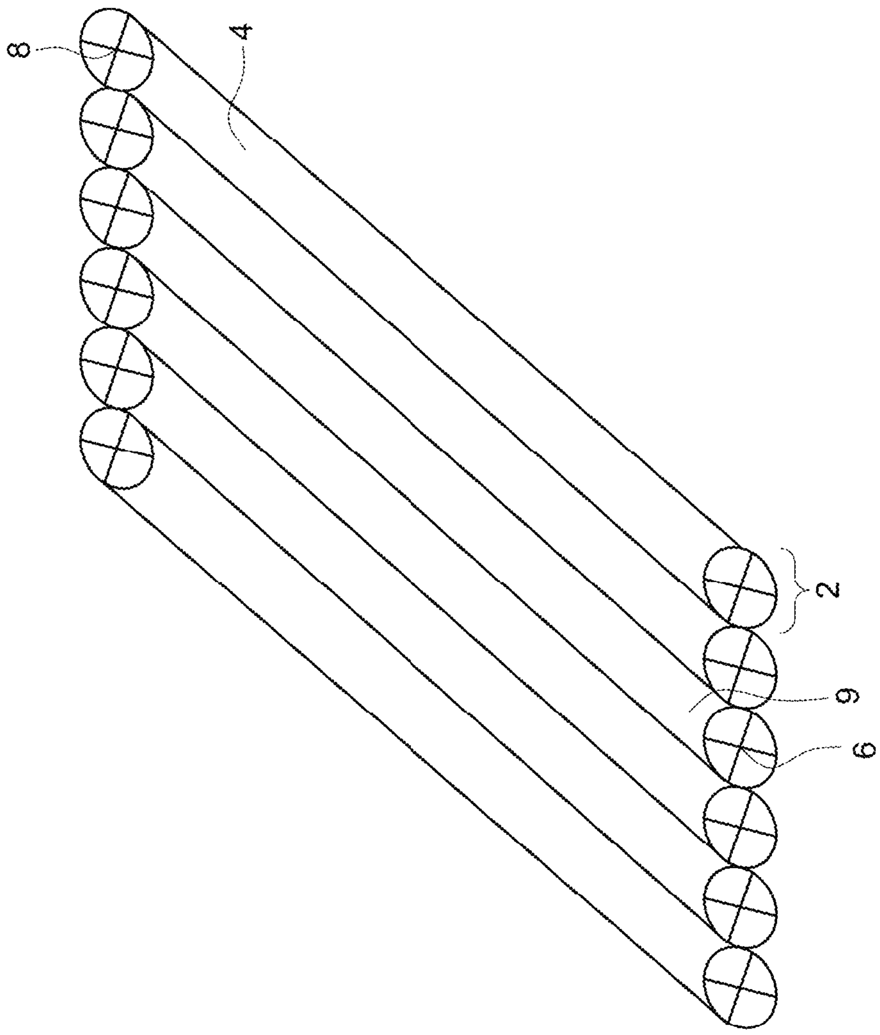
FIG. 23. Basic hermetic reactor (1) with cylindrical channels (4), walls/baffles (9), front valves (6) and back valves (8) and a gas permeable membrane (2).

In yet other systems, separate gas permeable membranes are used for ingress and egress of gases. FIG. 22 illustrates such a system. In this instance, two different gas permeable membranes (2, 50) feed into separate gas collection channels (30, 40) and are present over a single reactor channel (4). This type of system allows ingress, egress, and/or collection and/or separation of distinct useful gases. As an example, one membrane might be calibrated for oxygen passage and the second membrane calibrated for carbon dioxide or hydrogen passage or other relevant gas systems.

The reactor (1) produces a biofilm-biomat that serves as a food source, such as a protein source and/or an oil source. However, the biofilm-biomat can also serve as a leather analog, a bioplastic, a source of biofuel precursors, a biofuel, and/or combinations thereof. In yet other embodiments, the biofilm-biomat serves to produce organic products such as organic acids, antibiotics, enzymes, hormones, lipids, mycotoxins, vitamins, pigments and recombinant heterologous proteins.

The disclosed biofilm-biomat reactor fermentation technology enables growth on standard as well as extreme feedstocks and media, such as human waste (urine/feces), and produces a highly consolidated and textured product without the requirement of a separation or concentration step. Relatively high biomass production rates (0.55 g/L/h dry biomass) and high culture densities (100-180 g/L) are achieved without the need for active aeration or agitation. Scale-up of the system vertically, horizontally, and/or in more than two dimensions is simple and does not result in decreased productivity. The produced biofilm-biomats are typically 0.2 to 2.5 cm thick with a dry matter content of 10-30% and can be readily used for mission critical needs such as meat alternatives, a myriad of other appetizing foods, and building materials.

The fungal biofilm-biomats grown in the disclosed reactor system are described as pellicles, which in many ways are similar to the microbial biofilms that grow on surfaces, but are suspended in liquid culture at the gas-liquid interface. For example, bacterial cells within biofilms have been shown to withstand extreme disinfection treatments with sodium hypochlorite (bleach) and sodium hydroxide (Corcoran, 2013). The disclosed reactor system takes advantage of the biofilm structure, enabling growth on harsh human and industrial wastes and by-products that may be generated under extreme conditions such as those generated on space missions or by other harsh conditions caused by natural disasters.

The disclosed reactor design incorporates a gas-permeable membrane that sits directly on or suspended just above the liquid surface. The encapsulated reactor design allows for gas exchange with the exterior atmosphere but is hermetically sealed to keep contaminants from entering or gases/liquids from escaping. The encapsulated reactor design can also enable separation of consumable gases from evolved gases by way of gas permeable membrane. To accomplish this, in some instances valves and/or additional porous membranes having the same or different properties are used to form distinct layers between various aspects of the one or more feedstocks and optional liquid culture media.

Figure 17:
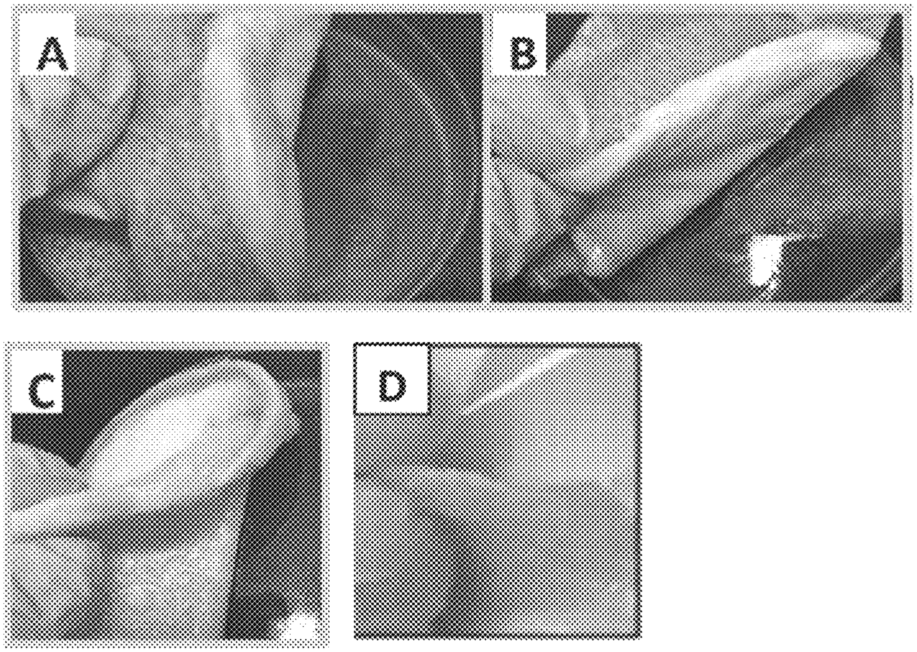
FIG. 17. *Fusarium oxysporum* strain MK7 biomats grown in five days under static conditions in Petri dishes covered with semi-permeable membranes constructed with (A)-(C) polypropylene and (D) polycarbonate. Essentially no free liquid remained in the Petri dish and all nutrients were incorporated into the biomat. The void/liquid volume of the reactor was essentially filled with biomat.

Rapid biofilm-biomat growth using the disclosed reactor design has been demonstrated with a variety of gas-permeable membrane materials. FIG. 17 shows an approximately 7 mm thick biomat grown in reactor where the container was a Petri dish covered with a polypropylene membrane which was laid directly on the feedstock/liquid medium surface. The initial biofilm formed by direct attachment to the membrane and grew downward into the liquid medium over time (see FIG. 16). By the end of a five-day growth period, essentially all of the feedstock/liquid medium was consumed and dense biomass completely filled the volume underneath the membrane.

The biomat produced only mildly adheres to the membrane and was easily harvested by simply peeling away the biomat from the membrane (see FIG. 17A-D). Additional experiments with polycarbonate membranes have produced similar results (data not shown). Thus, the total reactor volume can be efficiently utilized to produce dense, easily harvested biomass.

The biofilm-biomats commonly produced in the disclosed reactors are consolidated (110-180 g/L) and, depending on the fungus and growth conditions, exhibit a fibrous texture. Production of a fibrous biomass can be crucial for certain mission critical products such as foods that require texture to simulate meat, as well as fibrous materials that simulate leather and wood. The consolidated nature of the biomass also enables easy harvesting without the need for a concentration step (e.g., centrifugation, filtration).

Use of the Biofilm-Biomat Reactors in Zero Gravity

The primary physical force controlling formation and growth of the biofilm-biomat in the disclosed reactor is attachment to the membrane. Without being bound by theory, it is believed that grown in the disclosed reactor will not be impacted by the zero-gravity conditions experienced during space flight. Gravity driven directional growth or growth controlled by physical mixing or flow is not the overriding factor in the system, as it tends to be in gravity environments. Previous experiments in space successfully demonstrated fungal growth European Space Agency, Expeditions 25-28, Growth and Survival of Colored Fungi in Space (CFS-A)), providing an additional measure of confidence that the disclosed reactor system will function in a space environment.

For space missions and ease of deployment, freeze dried inoculum and essential ingredients to support growth on specific feedstocks (if needed) can be preloaded in the reactor.

Astronauts and space travelers can then prepare the feedstock, inoculum, and any media components. Incubation time is dependent on the feedstocks, the strain of microorganism, and other growth parameters such as pH, temperature and water content. The incubation conditions are simple in that fermentation is conducted under static conditions where the reactor is simply allowed to incubate in place. Dense consolidated biomats are harvested by simply opening the reactor closure (e.g. a Ziplock®-type) and removing the mats.

EXAMPLES

Example 1: Growth of Strain *Fusarium oxysporum* Strain MK7 and Other Fungi in Static Tray Reactors Filamentous acidophilic *Fusarium oxysporum* strain MK 7, *Ganoderma lucidum* (Reishi; FIG. 1A), *Pleurotus ostreatus* (pearl oyster, FIG. 1B: and blue oyster, FIG. 1C), *Sparassis crispa* (cauliflower; FIG. 1D), *Hypsizygus ulmarius* (elm oyster; FIG. 1E), *Calvatia gigantea* (giant puffball; FIG. 1F), and *Fusarium venenatum* biomats were grown in shallow static tray reactors as described in PCT/US2017/020050.

Example 2. Growth of *Fusarium oxysporum* Strain MK7 Biomat on Nutrient Medium Refreshed Daily (Semi-Static Conditions)

Dense *Fusarium oxysporum* strain MK7 biomats approximately 3 cm thick were grown in 21 days on nutrient medium that was refreshed daily. The biomats were generated using sterile MK7-1 liquid medium (described in PCT/US2017/020050) containing 7.5% glycerol at pH 3.0 in 12.7×17.8 cm Pyrex® glass trays. To initiate the experiment, 200 mLs of the nutrient medium was inoculated with 5% (volume/volume) of *Fusarium oxysporum* strain MK7 culture in the late exponential growth phase as described previously in PCT/US2017/020050. 200 mLs of the inoculated medium were added to each of three sterile trays that were lined with sterile coarse nylon mesh screens. The cultures were incubated undisturbed for 4 days at room temperature (~22° C.) to allow development of the initial biomat layer that formed at the surface of the liquid. After 4 days of growth, the biomats were gently lifted out of the tray using the nylon mesh screens and were tilted at a 45 degree angle to allow the liquid to drain out of the mats. The biomats were allowed to drain in this position until less than one drop of liquid dripped out every five seconds. Sufficient draining occurred, on average, after about 3 minutes.

Figure 2:
FIG. 2. Three-centimeter-thick biomat of *Fusarium oxysporum* strain MK7 that was formed in liquid nutrient medium that was refreshed daily (after day 4). Nylon mesh screen underneath the biomat is shown and used for lifting and moving the biomat to fresh medium.

The drip-dried biomats in their screens were placed in fresh preweighed 12.7×17.8 cm Pyrex® trays containing 200 mL of fresh MK7-glycerol medium (described in PCT/US2017/020050). Trays with biomats were re-weighed. The process of moving the biomats to another tray containing fresh medium was repeated on approximately a daily basis for 17 more days. Sampling of one of the biomats occurred on days 12, 15 and 21 and the moisture contents of these biomats were determined. The average moisture content of the biomats was 17.3% (std dev=0.7) and this value was used to calculate dry biomass production over the duration of the experiment. Dry biomass production was linear from day 4 through day 18 ($r^2$=0.995) after which biomass weight stabilized at about 2.5 Kg dry/$m^2$ (FIG. 1, y-axis normalized to a per $m^2$ basis, growth is typically exponential between day 0 and day 4). The average growth rate over this time period of linear growth was 6.04 g/$m^2$/h. FIG. 2 shows a ~3 cm thick biomat that developed after a total of 21 days growth using this method.

Example 3. Growth of Biomats Under Continuous Flow Conditions

Figure 3:
FIG. 3. Continuous flow system designed to continuously feed *Fusarium oxysporum* strain MK7 biomat growth and remove nutrients from media. White biomats shown in channels after 7 days of growth from the time of inoculation.

A continuous flow bioreactor system was fabricated to demonstrate growth of biomats on the surface of flowing liquid media. The system was fabricated from a 2.44 m long clear plastic roofing panel with a series of corrugations that were used as flow channels (FIG. 3). The ends of each of the channels were dammed with silicon (100% Silicone, DAP Products Inc., Baltimore, Md.) enabling liquid to be retained within the channels. Flow was facilitated through the channels by delivery of liquid media to one end of the channels via a peristaltic pump, with the liquid exiting the other end of the channels through holes in the bottom of the channels. The whole plastic roofing panel system was slanted at an angle of 1 cm rise per 1 m run to enable about 500 mL of liquid to be retained in each channel and a consistent flow being a function of the amount of liquid and the angle of the inclination.

The panel system was sanitized and wrapped in Saran®-like plastic wrap to isolate the system from the surrounding room environment. Sterile air was pumped under the plastic wrap at a rate of 400 mL/min creating a positive pressure on the system. To initiate development of a biomat prior to starting flow, a 500 mL volume of nutrient medium inoculated with the desired filamentous fungus was added per channel and allowed to incubate under quiescent/static conditions for 4 days. After 4 days, the peristaltic pump delivered a continuous pulsed flow of 400 mL/d to "feed" the biomats (ON at 2.016 mL/min for 49 min, 39 sec; OFF for 5 h 10 min 21 sec). Two independent experiments were conducted with each experiment using two separate flow channels as replicates (FIG. 3).

Figure 4:
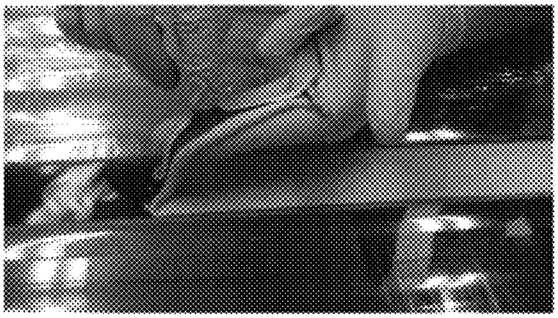
FIG. 4. Biomat growth after 10 days of growth from the time of inoculation (6 days under continuous flow +4 days under quiescent/static conditions).

Consolidated biomats were harvested after 10 days of growth on the nutrient medium (4 days under quiescent/static conditions followed by 6 days under continuous flow; FIG. 4). Average dry weight of the produced biomass was an average of 2.38 g for the replicate flow channels. During the continuous flow periods (day 4 to day 10) the average removal rates of C and N from the flowing liquid medium by the growing biomats were 11.9 and 1.2 mg/L/h, respectively. C and N removal rates from the liquid medium were determined by measuring liquid volume and total C and N inputs and outputs from the bioreactor system using a Costech total C and N analyzer (ECS 4010, Costech Analytical Technologies, Valencia, Calif.). Thus, the continuous flow system supported biomat growth at the surface. The experiments also served as a laboratory-scale demonstration for continuous feed of *Fusarium oxysporum* strain MK7 biomat growth and production of consolidated biomats. It should be noted that other feedstocks, flow rates and resulting growth rates can be achieved with this type of system. For example, with 10% glycerol in MK7-1 medium (described in PCT/US2017/020050) at pH 2.8, expected yields are greater than 40 grams dry biomass per day per $m^2$.

Figure 5:
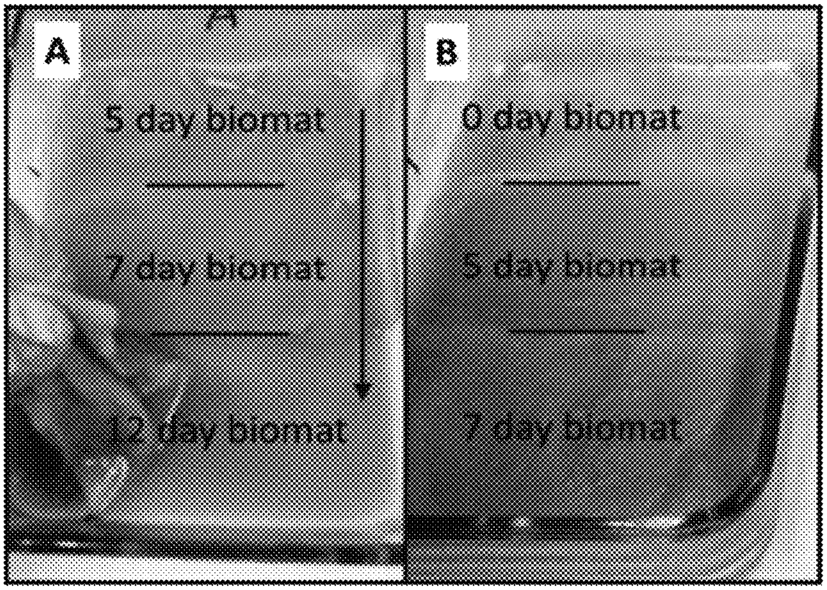
FIG. 5. Semi-continuous production of biomat showing (A) removal of the most mature portion of the biomat at day 12. After harvesting ⅓ of the most mature biomat at the lower end of the tray, the remaining biomat is physically moved down in the direction of the arrow until the edge of the biomat touches the end of the tray (B). Moving the biomat creates a fresh open space at the upper end of the tray where new biomat forms.
Figure 6:
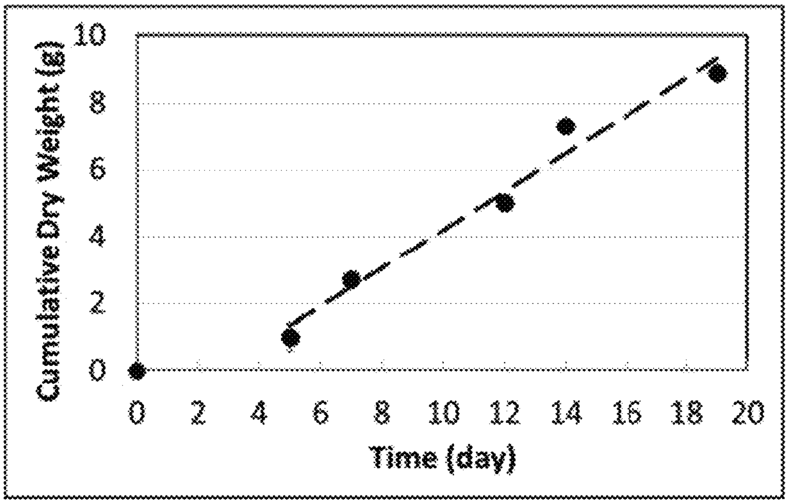
FIG. 6. Cumulative production of biomass over time using the semi-continuous production method. Dashed line is the linear regression line for day 5 through day 19 ($y=0.57x-1.52$, $r^2=0.973$). Error bars are standard deviations of the mean of three replicate trays. Error bars are not visible when smaller than data point symbol.

Example 4. Semi-Continuous and Continuous Production of *Fusarium oxysporum* Strain MK7 Biomats Dense *Fusarium oxysporum* strain MK7 biomats were grown and harvested on a semi-continuous basis over a period of 19 days. The biomats were generated using acid whey as the feedstock/carbon source supplemented with ½ strength MK7-1 medium salts (described in PCT/US2017/020050) adjusted to pH 4.0. To initiate the experiment, 200 mL of the nutrient medium inoculated with *Fusarium oxysporum* strain MK7 (5% volume/volume) in the late exponential growth phase was added to sterilized 12.7×17.8 cm Pyrex® glass trays, which were then covered with Saran® wrap and incubated at room temperature. After 5 days of growth, ⅓ of the biomat from one end of the tray was removed by cutting and removing a 5.9×12.7 cm section of biomat (FIG. 5A). The remaining ⅔ of biomat was then physically moved over to the open area of medium that was created by removal of the ⅓ portion of biomat. The biomat was shifted by physically grasping it with sterile gloved fingers and pulling the biomat over until it touched the end of the tray to open medium with no formed biomat at the other end of the tray (FIG. 5B). The process of harvesting a ⅓ section of the most mature portion of the biomat and then moving the remaining ⅔ of biomat over the open area was repeated periodically. 50 mLs of medium were aseptically removed from the tray every 4 days and replaced with 50 mLs of fresh sterile medium (acid whey with ½strength MK7-1) to replenish the nutrients removed from the liquid medium by removal of the biomat. Dry biomass production using this method yielded 0.57 g/day per tray or 25.2 g/d/$m^2$ between days 5 and 19 (FIG. 6). Thus, a semi-continuous production system was demonstrated whereby the most mature end of the biomat was harvested at an average rate of 1.56 cm/day and fresh biomat growth was initiated in the open area of medium at the other end of the tray.

Figure 7:
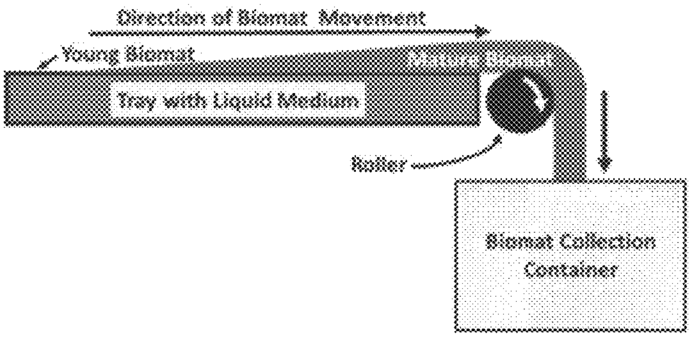
FIG. 7. Continuous production of biomat showing removal of the most mature portion of the biomat at the right. While continuously harvesting the most mature biomat at the right side of the tray, fresh open space is created at the left end of the tray enabling new biomat to form. Liquid medium in the tray can be replenished and/or augmented as required or continuously.

The system is also amenable to continuous harvesting and growth of a biomat whereby continuous removal is facilitated by a roller wheel that is attached to the mature end of the biomat (FIG. 7). The roller wheel slowly turns and harvests the mature biomat and at the same time creates an open medium for growth of new biomat at the other end of the tray. The roller wheel turns and harvests the biomat at a rate of 1.56 cm/day to reproduce the semi-continuous system described above. It is desirable that the nutrients in the liquid medium be replenished at the rate of nutrient removal by the biomat.

Example 5. Membrane Encapsulated Bioreactors

Dense *Fusarium oxysporum* strain MK7 biomats were grown in liquid growth medium that was encapsulated in a bioreactor system with no gas headspace. Sterile Petri dish bottoms (55 mm diameter) were filled to the brim with 57 mL of inoculated MK7-1 medium (described in PCT/US2017/020050) containing 8% glycerol. Gas permeable/semi-permeable membranes of polypropylene and polycarbonate were placed directly on the surface of the liquid medium and sealed tightly with rubber bands. No gas headspace was provided at the start of the growth period.

Figure 8:
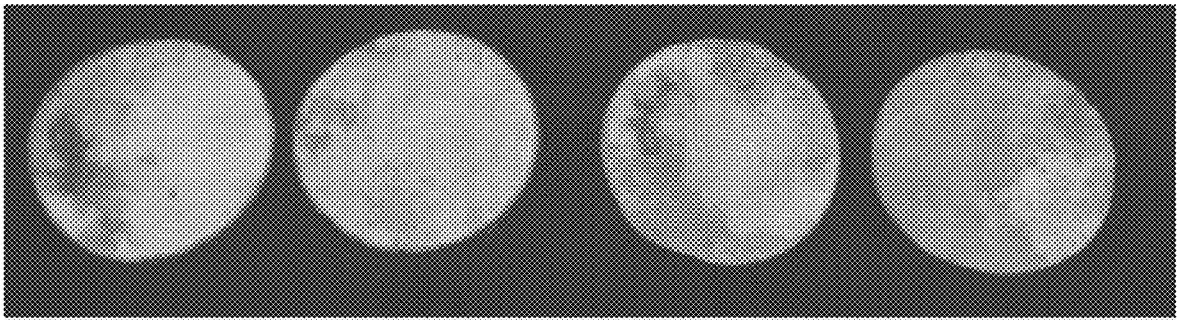
FIG. 8. Orange pigmentation of *Fusarium oxysporum* strain MK7 biomats (two excised disks at the right) after irradiation with UVB light for four hours. Two excised disks from non-irradiated control biomats are shown at the left.

After inoculating the medium and sealing the membranes, the bioreactors were allowed to sit undisturbed until harvest. FIG. 8 shows the ~5 mm and ~1 mm thick biomats of *Fusarium oxysporum* strain MK7 that grew directly underneath the polypropylene (FIG. 17A-C) and polycarbonate (FIG. 17 D) membranes in five days, respectively. The biomats mildly adhered to the membranes and could be easily harvested by simply peeling away the biomats from the membranes (FIG. 17).

Figure 9:
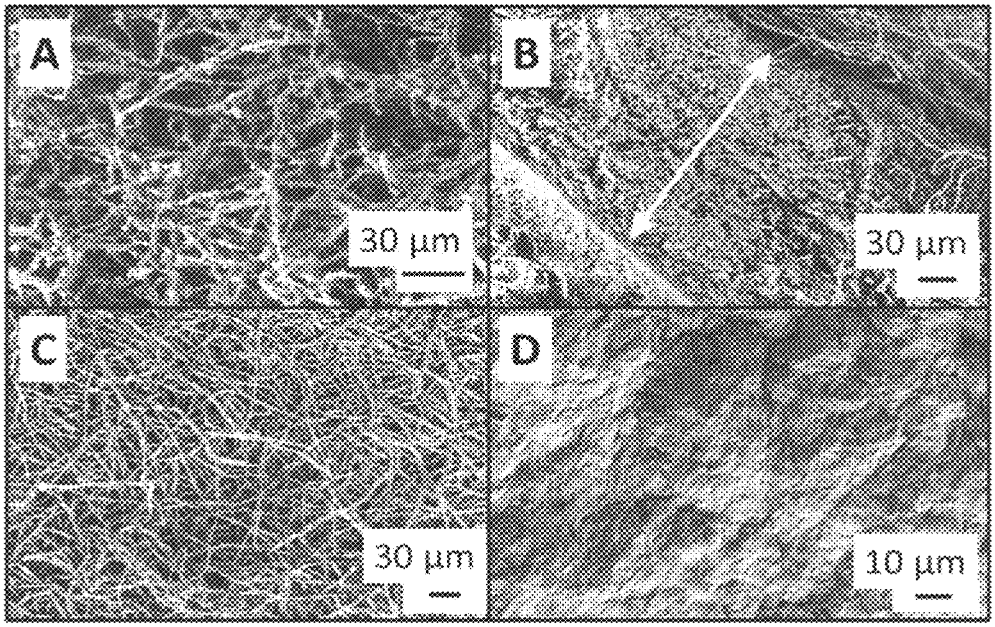
FIG. 9. Field emission scanning electron microscopy of 4 day old *Fusarium oxysporum* strain MK7 biomats produced using MK7-1 medium (described in PCT/US2017/020050) with glycerol, corn starch and corn steep liquor. Images A, B and C show biomat with EPS matrix removed by ethanol washing. A) View of top surface of biomat with aerial hyphae. B) Cross-section of the dense bottom layer with arrow delineating the layer. The cross-sectional view was created by cutting the biomat with a razor blade. The bottom of the biomat is shown at the bottom left corner of the image and the poorly adhering transition layer above the dense bottom layer is shown at the upper right corner. C) View of bottom surface of biomat. D) View of bottom surface of biomat with EPS matrix in place (i.e., EPS not removed with ethanol wash).

Example 6: Production of Pigments and Vitamin D2 by Irradiation of *Fusarium oxysporum* MK7 Biomats with UVB UVB light (290-320 nm) was used to trigger pigment production by *Fusarium oxysporum* strain MK7 biomats. *Fusarium oxysporum* strain MK7 biomats produced in 3 days on 7.5% glycerol MK7-1 medium (described in PCT/US2017/020050) were irradiated with UVB light for a period of 4 hours. The UVB light was emitted from a 50 W bulb (Slimline Desert 50 UVB T8 fluorescent bulb, 46 cm; Zilla, Franklin, Wis.) placed 10 cm above the biomat. Orange pigmentation was visually detected after 0.5 h of irradiation and was pronounced after 4 h of irradiation (FIG. 9). In addition, biomats that have not been exposed to UVB light have a vitamin D2 content of less than 50 IU/100 g of biomat whereas after UVB light exposure for approximately 12 hours the vitamin D2 content is increased to approximately 1.2 million IU/100 g biomat.

Example 7: *Fusarium oxysporum* Strain MK7 Biomats Grown on a Mixture of Glycerol, Starch and Corn Steep Liquor

*Fusarium oxysporum* strain MK7 biomats were produced from a mixture of glycerol, starch, corn steep liquor and MK7-1 salts (described in PCT/US2017/020050) in as little as 4 days. Glycerol was purchased from Duda Energy LLC (Decatur, Ala.; 99.7% Purity; USP Grade; Lot #466135376340); 100% Argo Corn Starch manufactured by Argo Food Companies, Inc (Memphis, Tenn.) was purchased from Albertson's supermarket in Bozeman, Mont., and the corn steep liquor was purchased from Santa Cruz Biotechnology, Inc. (Dallas, Tex.; Lot #B0116). The growth medium was a mixture of 7.5% glycerol (weight/weight), 2.5% starch and 2.5% corn steep liquor with MK7-1 salts. The mixture was adjusted to pH 3.3 by adding an appropriate amount of HCl and boiled for 15 minutes in a suitable container. After cooling to room temperature, the pH of the mixture was readjusted to 3.3 and then inoculated with 5% *Fusarium oxysporum* strain MK7 inoculum (vol/vol) as prepared in PCT/US2017/020050. Aliquots of 1.5 L inoculated media were added to three sanitized 0.25 $m^2$ polypropylene trays, placed in a sanitized tray rack system that was completely covered with aluminum foil to create dark conditions, and incubated at 23°±1° C. The filamentous fungal biomats that grew at the surface of the medium were harvested after 4 days by simply lifting the biomats from the trays.

The average final pH of the residual liquid in the three trays was 4.45 (standard deviation=0.14). Three 56.7 $cm^2$ circular portions were cut out and removed from each of the biomats at random positions and these portions were dried at 50° C. for 48 h to obtain dry weights. The average biomass dry weight (standard deviation) was 124.6 g/0.25 $m^2$ (43.4) or 498.4 g/$m^2$ (173.6). The mean thickness of the moist biomats were 7.5 mm and the mean density on a dry weight basis was 0.66 g/$cm^3$.

To expose the biomat filaments and enable examination by Field emission scanning electron microscopy (FE-SEM), the extracellular polymeric substances (EPS) between the filaments were removed by washing with ethanol. To accomplish this, 1 $cm^2$ portions (1 cm×1 cm) of the biomats were excised with a razor blade immediately before harvesting, and the excised portions were subjected to an ethanol washing/dehydration series by sequentially submersing the samples for the noted times in 40 mL of the ethanol mixtures as follows: 25% ethanol, 75% deionized $H_2O$ for 20 minutes; 50% ethanol, 50% deionized $H_2O$ for 20 minutes; 75% ethanol, 25% deionized $H_2O$ for 20 minutes; 95% ethanol, 5% deionized $H_2O$ for 20 minutes; 100% ethanol, 0% deionized $H_2O$ for 60 minutes. The 100% ethanol treatment was repeated 2 more times before storing the samples in 100% ethanol.

To retain microstructure integrity of the biomats for FE-SEM, ethanol washing/dehydration was followed by critical point drying using a Tousimis Samdri-795 critical point dryer according to the manufacturer instructions (Tousimis Samdri-795 Operations Manual; Tousimis, Rockville, Md.). After critical point drying, the samples were either mounted directly onto aluminum stubs or sliced into <0.3 mm thick sections with a razor blade prior to mounting. The samples were then coated with iridium (20 μm, EMITECH K575X, Electron Microscopy Sciences, Hatfield, Pa.) and examined with a JEOL 6100 FE-SEM using an incident beam energy of 1 keV (JEOL USA, Inc., Peabody, Mass.).

Figure 10:
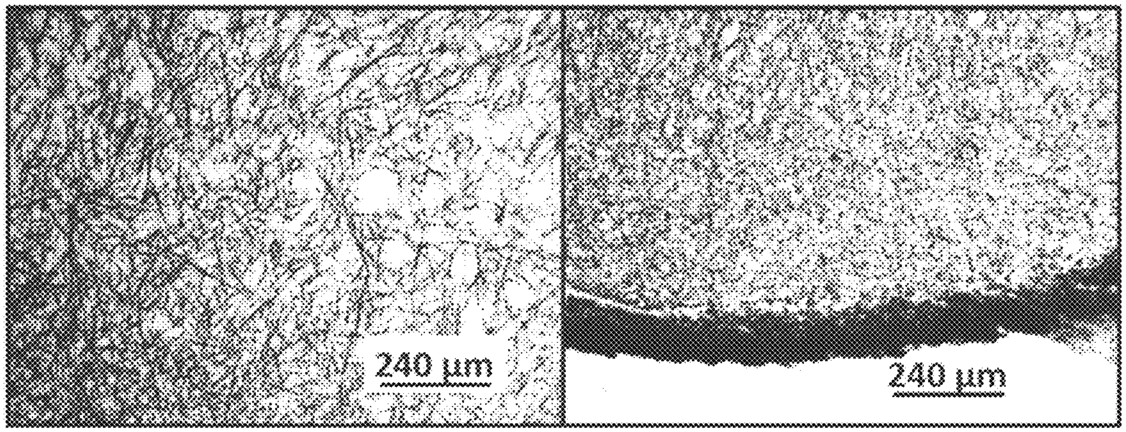
FIG. 10. Transmitted light microscope images (100×) of biomats grown on glycerol, starch and corn steep liquor. The image at the left of the aerial hyphal layer reveals the predominant near-vertical orientation of the filaments. The image at the right shows the dense bottom layer and the adjacent transitional layer.

FE-SEM imaging revealed a complex network of interwoven hyphal filaments (FIG. 10), very similar to the structure revealed by light microscopy for biomats grown on glycerol as reported in PCT/US2017/020050. Three distinct layers were observed: (a) an aerial hyphae layer at the top surface, (b) a dense bottom layer and (c) a transitional layer between the top and bottom layers. The transitional layer was only loosely attached to the dense bottom layer, thus enabling easy separation of the bottom layer from the rest of the biomat. Filament densities of the transitional layer ranged from slightly less dense than the bottom layer in the zone where the two layers met, to a density that was comparable to the aerial hyphae near the top of the biomat.

Excised samples were also prepared for light microscopy by slowly dipping into the following solutions in the order and times shown below:

Xylene, 3 min; Xylene, 3 min; 100% ethanol, 3 min; 100% ethanol, 3 min; 95% ethanol, 3 min; 95% ethanol, 3 min; 70% ethanol, 3 min; Deionized water, 3 min; Hematoxylin 1, 1.5 min; Running tap water rinse, 1 min; Clarifier solution, 1 min; Running tap water rinse, 1 min; Bluing solution, 1 min; Running tap water rinse, 1 min; 70% ethanol, 30 dips; 95% ethanol, 30 dips; 95% ethanol, 30 dips; 100% ethanol, 30 dips; 100% ethanol, 30 dips; 100% ethanol, 30 dips; Xylene, 30 dips; Xylene, 30 dips; Xylene, 30 dips; Apply cover slip.

Figure 11:
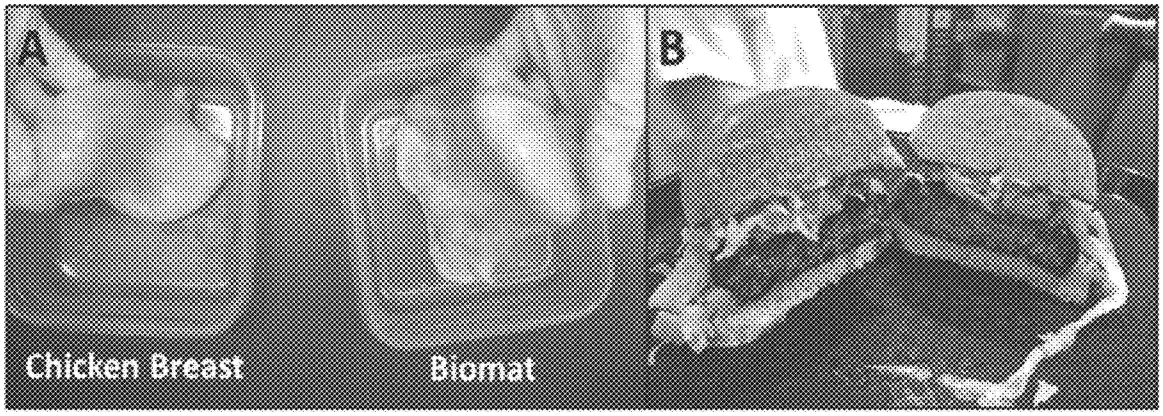
FIG. 11. A: Chicken breast on the left and fresh biomat with similar texture grown on glycerol on the right. B: "MycoBurger" prepared by renown chef Brooks Headley using fungal biomat.
Figure 12:
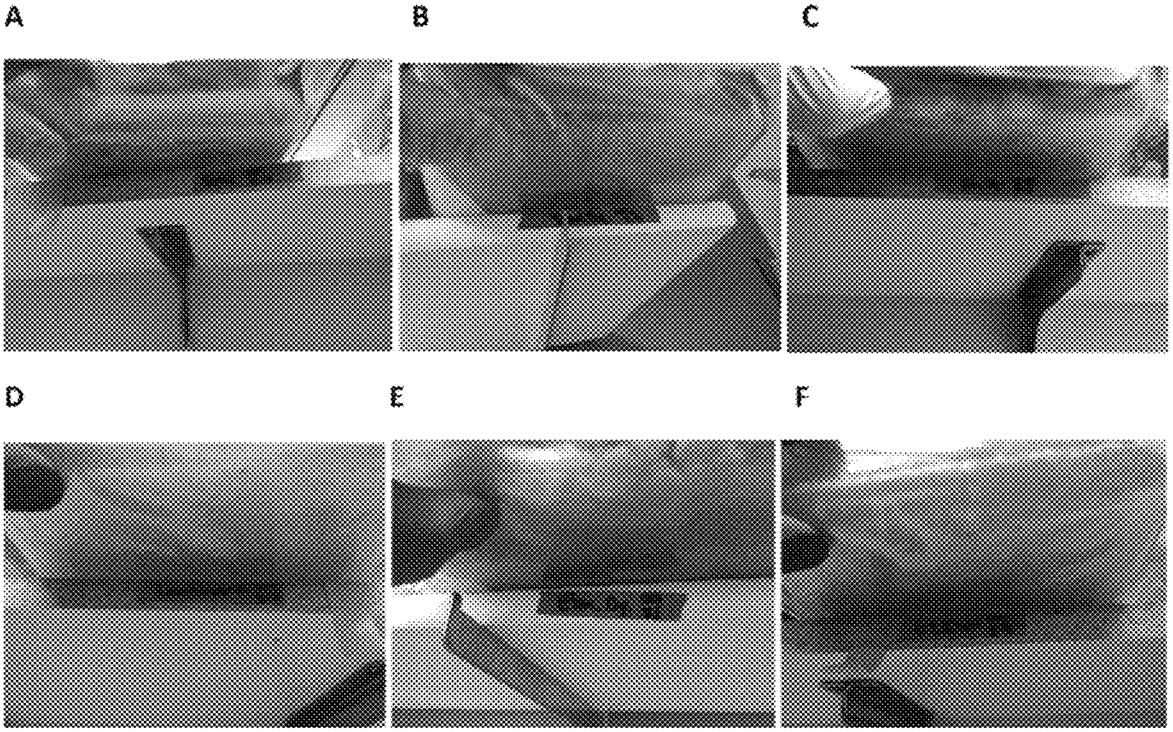
FIG. 12. Biomats produced using the disclosed method. A: Reishi mushroom; B: Pearl Oyster mushroom; C: Blue Oyster mushroom; D: Cauliflower mushroom; E: Elm oyster mushroom; F: Giant Puffball mushroom.

The above procedure was followed by visualization with a light microscope (B400B, Amscope, Irvine, Calif.) at 100× magnification (FIG. 11).

Sections of the biomats approximately 2 $cm^2$ in size were excised from the fresh biomats with a razor blade immediately before harvesting. These sections and then immersed in 35 mL of deionized water in 50 mL conical bottom centrifuge tubes. The tubes were sonicated (CP200T Ultrasonic Cleaner, Crest Ultrasonics, Ewing, N.J.) for either 0, 40, 90 or 150 seconds to disperse filaments into the liquid and enable microscopic observation. Aliquots of the liquid (—100 uL) from these tubes were placed on a glass slide, covered with a cover slip and observed with a light microscope (B400B, Amscope, Irvine, Calif.) at 100× magnification. The average length (std dev) of non-broken filaments were measured and determined to be 1.1 (0.6), 1.2 (0.4), 1.0 (0.4) and 1.2 (0.2) mm for the 0, 40, 90 and 160 second sonication treatments, respectively. The maximum filament length observed in each treatment were 2.5, 1.4, 1.8, and 1.4 mm, respectively. These filament lengths are significantly longer compared to growth of *Fusarium oxysporum* strain MK7 in submerged shake flask cultures where average lengths are less than 0.02 mm.

Example 8: Production of Chicken Nuggets Using *Fusarium oxysporum* Strain MK7 Biomats Grown on a Mixture of Glycerol, Starch and Corn Steep Liquor

Figure 13:
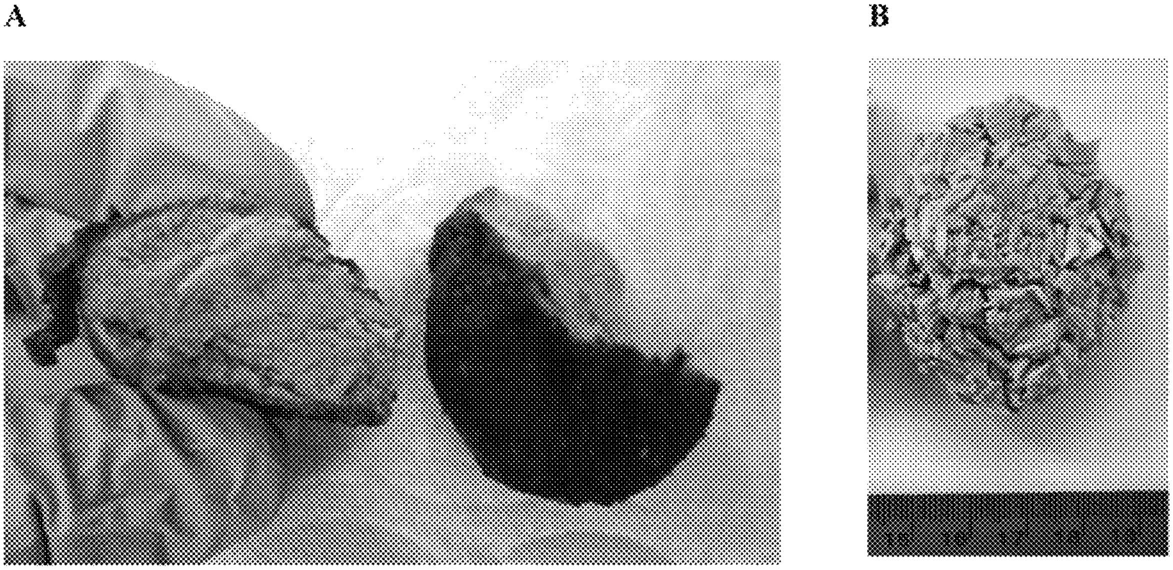
FIG. 13. A. Chicken nugget produced from *Fusarium oxysporum* strain MK7 biomat grown on a mixture of glycerol, starch and corn steep liquor. B. Chicken nugget produced from giant puffball biomat grown on malt media 001 (40 g malt, 4 g peptone, 1.2 g yeast extract, 20 drops/1 ml canola oil, 4 g ground oats, 1000 mL water).

*Fusarium oxysporum* strain MK7 biomat, produced as described above, were used to create chicken nuggets. Moist biomats were steamed in a pot steamer at 97° C. for 0.5 hour, cooled to room temperature and used as the base to produce chicken nuggets. Steamed moist biomat (200 g) was chopped into pieces less than 0.5 mm long and homogenized with 4% (weight/weight; 8 g) chicken base and 4% egg white protein (8 g). The resulting mixture comprised more than 90% *Fusarium oxysporum* strain MK7 biomat. Portions of this biomat mixture (~30 g) were formed into nugget shapes and steamed for in a pot steamer. The prepared nuggets were breaded by coating in egg whites and then mixing with bread crumbs that adhered to the surface prior to frying. The prepared nugget exhibited a chicken meat like texture (FIG. 13A) and exuded the typical aroma of chicken. Taste testing by 5 people deemed the nugget to closely simulate actual chicken containing chicken nuggets in terms of taste and texture.

Example 9: Production of *Fusarium oxysporum* Strain MK7 Biomat Extract

Highly concentrated and viscous extracts were produced from *Fusarium oxysporum* strain MK7 biomats. Biomats harvested after 4-16 days of cultivation, as previously described, are rinsed and steamed, drip dried on porous plastic mesh for 5 minutes, and placed in plastic bags and sealed. Sealed bags are frozen at either −20° C. or −80° C. for 24 hours prior to being incubated at 60° C. incubator in the original sealed bags for 48 hours after pH adjustment of the remaining medium liquid to between pH 4-6. After heat treatment, biomats are pressed through <1.5 mm pore size filters and the resulting liquid collected. The collected liquid is boiled for 10 minutes in a non-reactive vessel then dried at 60° C. until water content is ~6-8%, forming a sticky paste extract. The nutritional value of the extract is similar to the nutritional value of the steamed biomat and flour made from steamed biomats.

Example 10. Production of Yogurt from *Fusarium oxysporum* Strain MK7 Biomats Grown on Acid Whey

*Fusarium oxysporum* strain MK7 biomats were used directly to produce yogurt. The biomats were grown in trays on an acid whey feedstock/carbon source that was generated as a by-product of Greek yogurt manufacture, harvested after 6 days and were steamed within 20 minutes of harvesting. 200 g of the cooled, moist biomass was blended together with 600 g of drinking quality tap water to produce a milk-like suspension referred to as "MK7 liquid dispersion." The MK7 liquid dispersion was used as an ingredient by itself or in combination with cow's milk to produce yogurt.

Three mixtures containing different ratios of MK7 liquid dispersion to whole milk were prepared: 1) 25% MK7 liquid dispersion: 75% whole milk, 2) 50% MK7 liquid dispersion: 50% whole milk, and 3) 100% MK7 liquid dispersion. The mixtures were used to make three batches of yogurt by heating each mixture to 83° C. and holding at that temperature for 14 minutes with constant stirring. The mixtures were allowed to cool to 43° C. and then live yogurt cultures added as inoculum. The resulting mixture was incubated at 44° C. in a yogurt maker (Model YM80; EuroCuisine, Los Angeles, Calif.) for 8 hours. All of the resultant mixtures had the appearance and texture of yogurt (FIG. 14), as well as a smell and taste similar to typical yogurt.

Example 11: Growth of Mushroom Biomats on Glycerol

Biomass biomats comprised of Baby Bella Brown Crimini Mushrooms (*Agaricus bisporus*) and White Mushrooms were produced in as little as 10 days using glycerol as the primary carbon source (feedstock). These common edible mushrooms were purchased from Albertson's supermarket in Bozeman, Mont. and stored at 4° C. The medium used to grow the mushrooms consisted of 1 L of 7.5% glycerol with MK7-1 salts (described in PCT/US2017/020050) that was boiled for 10 minutes followed by cooling to room temperature (~23° C.). The pH of the mixture was adjusted to 2.7 and 200 mL of the pH adjusted mixture was poured in two sterile 12.7×17.8 cm Pyrex® trays. The inoculum consisted of 5 g of blended, surface-sterilized Crimini or White Mushrooms that was added to the medium in each tray. The mushroom inoculum was prepared as follows: 1) 10 g of moist Crimini or White Mushrooms were added to 200 mL of a 5% bleach solution and the suspension was stirred for 2 minutes to surface sterilize the mushrooms, 2) the mushrooms were then rinsed by transferring into 200 mL of sterile glycerol/MK7-1 salts medium (described in PCT/US2017/020050) and stirring for 2 minutes, 3) the surface sterilized mushrooms were blended for 30 seconds in a coffee grinder that had been sterilized by rinsing with 70% ethanol, 4) the ground mushroom biomass (<5 mm long aggregates) was surface sterilized again by repeating steps 1 and 2 with the ground biomass, 5) 5 grams of the ground mushroom biomass was added to the liquid medium in the Pyrex® trays (final pH=4.0-4.1 after addition of mushrooms), and 6) the trays were covered and allowed to incubate at room temperature (22±2° C.) in the dark.

Biomats were observed to develop on the surface of the medium after 3 days of incubation and consolidated biomats were harvested after 10 days of growth. Biomats of Crimini Mushrooms covered the entire surface of the liquid medium in the tray while biomat growth of White Mushrooms covered approximately ½ the liquid medium as five floating biomat islands. The mean thickness of the biomats were 1.5 mm for the Crimini and 1.7 mm for the White Mushrooms. Biomass biomats were dried at 50° C. for 48 h and the dry weights produced per tray were 1.14 g and 2.12 g for the Crimini and White Mushrooms, respectively. Densities on a dry weight basis for the dry biomass biomats were 0.033 and 0.111 g/cm$^3$ for the Crimini and White Mushrooms, respectively.

Microscope images revealed the mycelial nature of the biomats. Average hyphal thicknesses were 25.2 μm (std dev=6.2) and 18.7 μm (4.0) for the Crimini and White Mushroom biomats, respectively.

Produced Crimini biomats were used to create chicken nuggets. Biomats were steamed at 97° C. for 0.5 hour, cooled to room temperature and used as the base to produce chicken nuggets. Steamed moist biomass (2.5 g) was mixed with 3% (weight/weight; 75 mg) Better Than Bouillon chicken base (Southeastern Mills, Inc. Rome, Ga.) and 3% Eggwhite Protein (75 mg; Now Foods, Bloomingdale, Ill.) and chopped into pieces less than 2 mm long using a razor blade. The mixture was formed into a nugget and steamed for 0.5 hour. The prepared nugget provided the typical aroma of chicken with a slight mushroom fragrance. When tasted, the nugget had a chicken to neutral flavor.

Example 12. Growth of Mushroom Biomats on Malt and Glycerol Media

Biomass biomats comprised of *Calvatia gigantean* (giant puffball), *Pleurotus ostreatus* (pearl oyster), *Pleurotus ostreatus* var. columbinus (blue oyster), *Hypsizygus ulmarius* (elm oyster), *Sparassis crispa* (cauliflower) and *Ganoderma lucidum* (reishi) were produced in as little as 5 days using Malt Extract Medium 001, Glycerol Medium 002, Hansen's Medium, MK7-SF Medium, Malt Extract+$NH_4NO_3$ Medium 003 (Table 3). All final media contained 0.01% chloramphenicol.

TABLE 3

| Ingredients added to deionized or drinking quality tap water to prepare nutrient media. | | | | | | |
|---|---|---|---|---|---|---|
| Ingredient | Amount | | Grade | Lot # | Vendor | Location |
| Malt Extract Medium 001 | | | | | | |
| Light Pilsner Malt | 40.0 | g | Food | 180526B | Homebrewstuff.com | Boise, ID |
| Peptone | 4.0 | g | Research | 44984-57374 | Research Products International | Mt. Prospect, IL |
| Yeast Extract Powder | 1.2 | g | Research | 53852-66581 | Research Products International | Mt. Prospect, IL |
| Canola Oil | 1.0 | mL | Food | Sep. 25, 2019 CA S3283 | Better Living LLC | Pleasanton, CA |
| Ground Oats | 4.0 | g | Food | Jan. 25, 2020 I2M 06:36 | Walmart-Stores, Inc | Bentonville, AR |
| Tap $H_2O$ | 1000 | mL | N/A | N/A | N/a | Bozeman, MT |
| Glycerol Medium 002 | | | | | | |
| Glycerol | 40.0 | g | Food/USP | 20149018137001 | Duda Energy LLC | Decatur, AL |
| Peptone | 4.0 | g | Reagent | 44984-57374 | Research Products | Mt. Prospect, IL |
| Yeast Extract Powder | 1.2 | g | Reagent | 53852-66581 | Research Products International | Mt. Prospect, IL |
| Canola Oil | 1.0 | mL | Food | Sep. 25, 2019 CA S3283 | Better Living LLC | Pleasanton, CA |
| Ground Oats | 4.0 | g | Food | Jan. 25, 2020 I2M 06:36 | Walmart-Stores, Inc | Bentonville, AR |
| Tap $H_2O$ | 1000 | mL | N/A | N/A | N/a | Bozeman, MT |
| Hansen's Medium | | | | | | |
| Peptone | 1.0 | g | Reagent | 44984-57374 | Research Products International | Mt. Prospect, IL |
| $KH_2PO_4$ * $7H_2O$ | 0.3 | g | Reagent | Mfg. Doesn't use lot numbers | Eisen-Golden Laboratories | Dublin, CA |
| $MgSO_4$ * $7H_2O$ | 2.0 | g | USP | 81721 | San Francisco Salt Co. | San Leandro, CA |
| Glucose | 5.0 | g | Reagent | 0435C235 | Fisher Scientific | Denver, CO |
| Tap $H_2O$ | 1000 | mL | N/A | N/A | N/a | Bozeman, MT |
| MK7-SF Medium | | | | | | |
| $NH_4NO_3$ | 7.553 | g | ACS | A0390194 | Acros Organics | Somerville, NJ |
| Urea | 2.548 | g | USP | 30570-67229 | Research Products | Mt. Prospect, IL |
| $CaCl_2$ | 2.000 | g | Reagent | 102615 | Fritz Pro Aquatics | Mesquite, TX |
| $MgSO_4$ * $7H_2O$ | 2.000 | g | USP | 81721 | San Francisco Salt Co. | San Leandro, CA |
| $KH_2PO_4$ | 7.500 | g | Reagent | Mfg. Doesn't use lot numbers | Eisen-Golden Laboratories | Dublin, CA |
| Trace * | 2.000 | mL | * | * | * | * |
| Glycerol | 0.075 | Kg | Food/USP | 20149018137001 | Duda Energy LLC | Decatur, AL |
| Yeast Exract | 1.750 | g | Research | 53852-66581 | Research Products International | Mt. Prospect, IL |
| $FeCL_2$ * $4H_2O$ | 0.020 | g | Reagent | 951164 | Fisher Scientific | Fair Lawn, NJ |
| DI $H_2O$ | 0.940 | L | N/A | N/A | N/A | Bozeman, MT |

| Trace Components * | | | | | |
|---|---|---|---|---|---|
| Micronutrients * | mg/L | Grade | Lot # | Vendor | Location |
| FeSO4•7 H2O | 9.98 | ACS | 3562C398 | Amresco | Solon, OH |
| ZnSO4•7 H2O | 4.4 | USP/FCC | 61641 | Fisher | Waltham, MA |
| MnCl2•4 H2O | 1.01 | Reagent | 13446-34-9 | Fisher | Waltham, MA |
| CoCl2•6 H2O | 0.32 | Reagent | 7791-13-1 | Fisher | Waltham, MA |
| CuSO4•5 H2O | 0.31 | Technical | 114675 | Fisher | Waltham, MA |
| (NH4)6Mo7O24•4H2O | 0.22 | ACS | 68H0004 | Sigma | St. Louis, MO |
| H3BO3 | 0.23 | ACS | 103289 | Fisher | Waltham, MA |
| EDTA, free acid | 78.52 | Electrophoresis | 46187 | Fisher | Waltham, MA |

TABLE 3-continued

| Ingredients added to deionized or drinking quality tap water to prepare nutrient media. | | | | | |
|---|---|---|---|---|---|
| Malt Extract + NH4NO3 Medium 003 | | | | | |
| Ingredient | Amount | Grade | Lot # | Vendor | Location |
| NH4NO3 | 5.0 g | ACS | A0390194 | Acros Organics | Somerville, NJ |
| Light Pilsner Malt | 40.0 g | Food | 180526B | Homebrewstuff.com | Boise, ID |
| Peptone | 4.0 g | Research | 44984-57374 | Research Products International | Mt. Prospect, IL |
| Yeast Extract Powder | 1.2 g | Research | 53852-66581 | Research Products International | Mt. Prospect, IL |
| Canola Oil | 1.0 mL | Food | SEP. 25, 2019 CA S3283 | Better Living LLC | Pleasanton, CA |
| Ground Oats | 4.0 g | Food | Jan. 25, 2020 I2M 06:36 | Walmart-Stores, Inc | Bentonville, AR |
| Tap $H_2O$ | 1000 mL | N/A | N/A | N/A | Bozeman, MT |

The above recipes in Table 3 were used to prepare media in either 2 L Pyrex® bottles or 8 L stainless steel pots by mixing the specified ingredients into the specific volumes of water depending on the volume of media desired. Ingredients were added to water while liquid was continuously stirred with a stir bar or a spoon. Each component of the media was thoroughly mixed into the liquid before the next component was added, pH for the MK7-SF medium was adjusted to 5.0, and the solutions autoclaved. All other pH's resulted from simply mixing the ingredients. The medium and vessels were autoclaved for at least 20 minutes at 20 psi and 121° C. Osmotic pressure of the liquid was measured using an Advanced Instruments, Inc. osmometer Model 3250 (Two Technology Way, Norwood, Mass.).

After autoclaving, the media were allowed to cool to room to temperature and individual vessels were inoculated with the mushroom species shown in Table 4.

TABLE 4

| Mushroom spores (10 cc syringes) were purchased from MycoDirect (12172 Route 47, Ste 199 Huntley, Il 60142) and received on Aug. 2, 2018. Elm Oyster spores were purchased from Everything Mushrooms (1004 Sevier Ave Knoxville, TN 37920) and received on Aug. 3, 2018. | | |
|---|---|---|
| | Lot | Date Produced by Company |
| Blue Oyster | 3-P7 | February 2018 |
| Pearl Oyster | 9P8 | December 2017 |
| Giant Puffball | N/A | March 2018 |
| Cauliflower Mushroom | N/A | April 2018 |
| Elm Oyster (1 cc dried) | N/A | October 2017 |

Inoculation of growth media was preformed using the following methods applied using aseptic technique. All aseptic work in these experiments were performed in Class II biosafety cabinet. Spore syringes were used to directly inoculate approximately 75 mL of growth medium in previously autoclaved, 12.7×17.8 cm Pyrex® glass trays. This was done by aseptically transferring liquid medium into an autoclaved Pyrex® tray and inoculating with 2 cc of the suspension contained in the spore syringe. The tray was covered with sterile aluminum foil and then gently swirled to mix the inoculated medium.

Malt Extract Agar (MEA; Table 5) plates were prepared aseptically by autoclaving MEA, allowing to cool to 50° C., and pouring ~25 mL into 100×15 mm sterile Petri dishes.

TABLE 5

| Ingredients used to prepare Malt Extract Agar Malt Extract Media (MEA) | | | | | |
|---|---|---|---|---|---|
| Ingredient | Amount | Grade | Lot # | Vendor | Location |
| Light Pilsner Malt | 30.0 g | Food | 180526B | Homebrewstuff.com | Boise, ID |
| Agar | 20.0 g | Microbiological | 2170501 | BD | Sparks, MD |
| Tap $H_2O$ | 1000 mL | N/A | N/A | N/A | Bozeman, MT |

MEA plates were inoculated by aliquoting 1 cc of liquid from the suspension contained within the spore syringe onto the plates. The agar plates were then sealed with Parafilm® and placed into a clean dark drawer at room temperature.

After mycelium had covered the entire surface of the MEA plates, they were used for inoculation of 1.5 L medium in 2 L baffled shaker flasks. Approximately 2 $cm^2$ portions of agar medium with mycelium on the surface were excised from the plates with a sterile razor blade and diced into ~2 $mm^2$ portions, which were then added to two flasks containing 1.5 L of Malt Extract 001 medium. The medium was incubated for 3 days at room temperature (23±1° C.) with intermittent shaking by hand (flasks were vigorously shaken by hand for 1 minute at a minimum of five times per day).

The cultures in the shaker flasks were then used as inoculum for 6 L of Malt Extract medium 001 and for 6 L of Malt Extract+$NH_4NO_3$ 003 medium. The media were inoculated with 15% (vol:vol) of inoculum culture and mixed thoroughly. Two liters of inoculated media were poured into each of three 0.25 $m^2$ plastic trays that were placed into a tray rack. The racks were wrapped in Saran® and allowed to incubate for 6 days. Relatively dense biomats covering the entire surface within 4 days and the biomats were harvested after 6 days.

Biomats from 12.7×17.8 cm Pyrex® glass trays and the 0.25 $m^2$ plastic trays were harvested by lifting the biomats from the trays and gently squeezing by hand. Portions of the biomats (3-50 g) were streamed for 20 minutes over boiling water (~5 cm above surface of water) in a pot steamer set on a kitchen oven burner. After steaming, the biomass was allowed to cool to room temperature and immediately bagged in a Ziploc® bag and sent to Eurofins (Des Moines, Iowa) for protein analysis (N by combustion, Test Code QD252).

MK7 up to 20%, oftentimes in a ratio of 10 *Fusarium oxysporum* strain MK7:1 spice mix, with or without additional ingredients such as onion, binders, and a fat such as cocoa butter. The mixture is then fried to remove an appropriate amount of moisture. Additional ingredients can then be added, such as bulgur, vegetable broth, potatoes, etc. prior to shaping in the desired shape and cooking.

TABLE 6

Results from a series of Giant Puffball growth in trays in various types of media

| Media | Tray Size ($m^2$) | pH Initial Media | C:N | Ionic Strength (mmol/L) | Osmotic Pressure (mOsm) | Time (days) | Final pH Free Liquid | Protein (%) | Biomass per Surface Area ($g/m^2$) | Density ($g/cm^3$) | Tensile Strength of Wet Biomat ($g/cm^3$) |
|---|---|---|---|---|---|---|---|---|---|---|---|
| Malt 001 | 0.022 | 6.28 | 19 | 33.1 | 169 | 5.7 | 5.62 | 32.03 | 71.4 | 0.057 | 314.1 |
| Glycerol 002 | 0.022 | 6.96 | 30 | 13.6 | 505 | 5.7 | 5.54 | N/A | 40 | 0.04 | 214.9 |
| Hansen's | 0.022 | 8.81 | 27 | 30.7 | 39 | N/A | N/A | N/A | N/A | N/A | N/A |
| MK7-SF | 0.022 | 4.91 | 7.5 | 344 | 1387 | 9.0 | 5.07 | 46.33 | 178.6 | 0.045 | 135.0 |
| Malt 001 | 0.25 | 6.96 | 19 | 33.1 | 169 | 6.2 | 6.25 | 32.04 | 111.1 | 0.037 | 264.0 |
| Malt + $NH_4NO_3$ 003 | 0.25 | 6.88 | 7.5 | 145.1 | 287 | 5.8 | N/A | 46.88 | 108.3 | 0.11 | 281.1 |

Example 13. *Fusarium oxysporum* Strain MK7 Chicken Nugget

Chicken flavored *Fusarium oxysporum* strain MK7 is a basic ingredient to a number of recipes including chicken nuggets, with or without breading, chicken for Asian dishes, or other chicken dishes as a chicken replacement. *Fusarium oxysporum* strain MK7 biomats produced from different feedstocks/carbon sources result in slightly different chicken flavors. The glycerol chicken is sweeter and the acid whey chicken tends to be a little bit sourer.

The amount of food processing and the blade used (i.e. sharp metal blade, dull metal blade, plastic blade) result in different chicken nugget textures. Further, acceptable chicken nuggets can be produced from a wide variety of biomass sizes. That is, biomass can be cut with a knife, lightly food processed or highly food processed and still result in acceptable chicken analogs.

A 5020:1:1 ratio of *Fusarium oxysporum* strain MK7: chicken stock:binder was used with or without approximately a 66.6% *Fusarium oxysporum* strain MK7:fat ratio. Suitable fats include duck fat, coconut butter, and cocoa butter. After mixing, the mixture is steamed for approximately 30 minutes to set the binder; however, some binders may require more or less time. Additional breading can then be added and the resulting nuggets process as typical for such foodstuffs.

Example 14: Breakfast Sausage and/or Hot Dog and/or Burger

An appropriate spice mix is added to size reduced *Fusarium oxysporum* strain MK7 biomats as needed to develop the flavors desired, which may be between 10 wt. % of spice mix to a quantity of *Fusarium oxysporum* strain

Example 15: Ice Cream and Mousse

Figure 14:
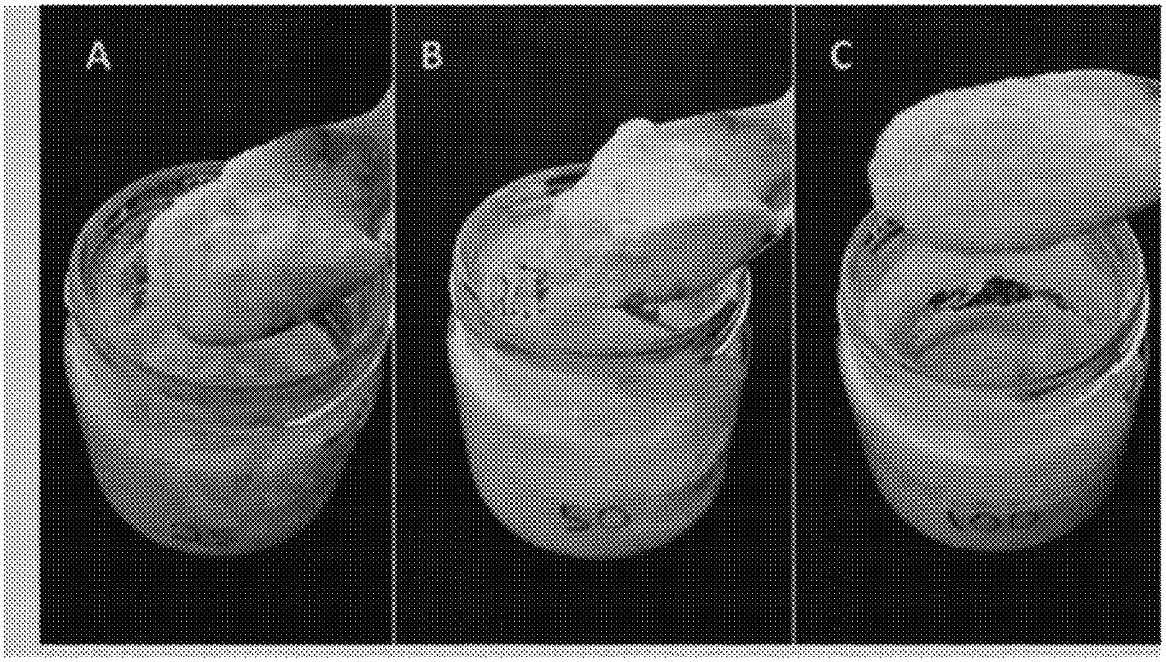
FIG. 14. Yogurt prepared from a live yogurt culture using A. 25% MK7 liquid dispersion: 75% whole milk, B. 50% MK7 liquid dispersion: 50% whole milk, and C. 100% MK7 liquid dispersion. The MK7 liquid dispersion used in these cultures was prepared from *Fusarium oxysporum* strain MK7 biomats grown on acid whey.
Figure 15:
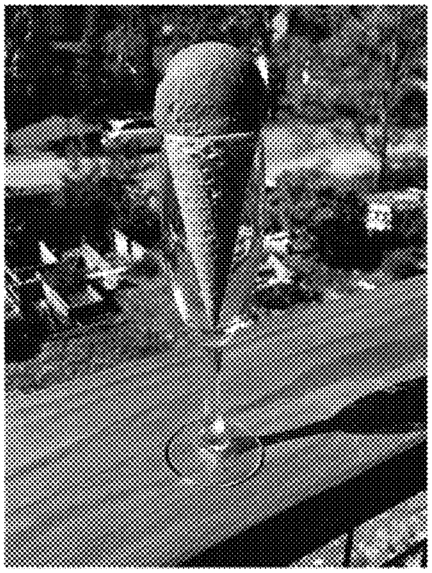
FIG. 15. Vegan ice cream analogue produced from *Fusarium oxysporum* strain MK7 biomats.

A ratio of approximately 1:3 *Fusarium oxysporum* strain MK7 biomat:water is generated having a particle size with average filament lengths less than 900 microns. This mixture is gently heated until there is no longer a fungal scent and then used in approximately a 4:1 ratio with cashews, optionally with an appropriate amount of xanthan gum and/or flavoring, to generate a mix which may be optionally heated and then cooled to form a mousse. For frozen dessert, the mix is then placed in an ice cream churner and, after churning, frozen to form a non-meltable frozen dessert (FIG. 14).

Example 16: Production of Truffle Oil from Truffle Biomats

Oil extract can be prepared from Truffle (*Tuber* sp.) biomats grown as described above. In one instance, truffle biomats were grown in trays in as little as 7 days using malt extract, glucose and peptone as the primary carbon sources (feedstock). The edible Truffle mushroom was purchased from IGB Trading LLC on the Amazon Marketplace and stored at 4° C. A pure culture of the *Tuber* sp. fungus was prepared from the purchased truffle by placing ~3 $mm^3$ portions of truffle (cut with a sterile razor blade) on Malt Extract Agar+0.01% chloramphenicol (used to inhibit bacterial growth). A Malt Extract Agar was prepared by mixing 20 g of malt extract, 20 g of glucose, 1 g peptone and 20 g of agar in 1 L of deionized water prior to autoclaving for 30 minutes and cooling to 50° C. before adding 0.01% chloramphenicol. The sterile mixture was then poured into 9 cm diameter Petri plates and allowed to cool and solidify.

The fungus was observed to grow on the trays after 3 days. After 4 days of growth, hyphae were picked with a sterile microbiological loop and streaked onto a fresh set of Malt Extract Agar+chloramphenicol plates. The fungus was allowed to grow on said plates for 5 days, after which hyphae were picked with a microbiological loop and used to confirm culture purity by DNA sequencing. Confirmation was accomplished by extracting and purifying the DNA (FastDNA Spin Kit, MP Biomedicals) and sequencing the ITS region of the metagenome followed by phylogenetic classification of the sequences using Blast (NCBI database).

Malt Extract Broth was prepared by mixing 20 g of malt extract, 20 g of glucose and 1 g peptone in 1 L of deionized water and sterilized. Scrapes of the hyphae with the microbiological loop were also used to inoculate 50 mL of sterile Malt Extract Broth in sterile baffled shaker flasks capped with sterile gauze material. Sterile gauze was used as it allowed exchange of gases into and out of the shaker flask. Shaker flasks were then rotated at 185 rpm for 5 days. The rotated cultures were then used to inoculate 350 mL of sterile Malt Extract Broth in sterile 12.7×17.8 cm Pyrex® glass trays. The inoculum density was for this culture medium was 7.5% inoculum to 92.5% broth. After 7 days of growth in the trays, the filamentous biomat formed on the surface was harvested by lifting the biomat from the liquid medium. The harvested biomats were dried at 40° C. for 48 h. Lipids/oil from these harvested biomats were extracted by either mechanical pressing or by solvent extraction using hexane, although other extraction methodologies can be used. Can also use another extraction method Yuval will send.

Example 17: MK7 Flour

*Fusarium oxysporum* strain MK7 biomat, produced as described above, was used to create dried powder similar in particle size and particle size distribution to a standard baking flour. Here, moist biomats were steamed in a pot steamer at 97° C. for 0.5 hour, cooled to room temperature and dehydrated in a Cuisinart dehydrator (model DHR-20) for 2-8 hours with an average dehydration time being 4 hours. Dehydration time is a function of the amount of biomass loaded into the dehydrator, distribution of biomats in the dehydrator which impacts air flow in the dehydrator and the water content of biomats (average water content approximately 75%) and room temperature. Water content post dehydration varies between 4 and 14% with average water content post dehydration being below 12%. Dehydrated biomass was size reduced using a coffee grinder (KRUPS, Electric coffee and spice grinder, stainless steel blades F2034251) until finely ground. Average particle size for ground biomat flour ranged from 75 microns to 120 microns. A small fraction of larger particles, app 5 wt %, had a particle size of greater than 180 microns. A small fraction of smaller particles, app. 5 wt % had a particle size smaller than 75 microns. Said smaller particles where off a size which enabled the small particles to remain air borne for extended periods of time. Particle size was determined by sifting 100 gram samples of size reduced biomats for 5 minutes in sieves with 180 μm, 120 μm and 75 μm openings. Water content post dehydration and post size reduction below 6% is preferred as higher water contents can lead to clumping of dried and milled biomass.

Biomat flour was then used as an addition to other standard flours (King Arthur flour, Bob's Red Mill Flour & Bob's Red Mill Wheat Flour) and a variety of baked goods where prepared. Biomat flour was loaded at 5 wt %, 10 wt %, 20 wt % and 30 wt % with no deleterious effect on ultimate baked good taste, rising, texture, appearance or smell. Products demonstrated included bread (7 grain, white & wheat), pastries (Pate a Choux), cookies, pasta and dumplings. The resulting products performed well in taste tests and the inclusion of MK7 flour was not detectable to those tasting the products.

Example 18: MK7 Extender

*Fusarium oxysporum* strain MK7 biomat, produced as described above, was used to create particles of biomass that were used as an addition to meat and fish as an extender (i.e. increase the amount of total food product by the addition of MK7 to other exiting foodstuffs). Moist biomats were steamed in a pot steamer at 97° C. for 0.5 hour, cooled to room temperature. Biomats where size reduced (i.e. chopping with a knife or food processing in a food processor) to a desirable particle size distribution. Size reduced biomass was then added to different food products to extend the amount of meat in the case of a meat extender or fish in the case of a fish extender. As an example of meat extension. 10%, 20%, 30%, 40% and 50% additions of size reduced biomass were added to hamburger meat. Size reduction of biomass was evaluated at a number of different size distributions. Smaller particle sizes tended to produce denser and creamier textures. Larger particles tended to produce products with more texture, more mouth feel and required more mastication before swallowing. The extended meat was them processed as though no biomass was added. In the case of hamburger extension, spices or binders can be optionally added and the extended meat was formed into a patty or meat ball and cooked until the meat was cooked to the consumer desired temperature. Cooking methods included stove top, oven, frying and grill. Taste tests showed that acceptable food products where produced at all loading levels and all size distributions of added biomass. Chicken and pork extensions where also tried at similar loading levels with similar cooking and tasting results.

Fish extension was also demonstrated at 10%, 20%, 30% and 40% loadings. Fish fillet and fish balls where produced by adding processed MK7 at a variety of different size distributions ranging from small particles (less than 1.0 mm) to large particles (greater than 2 mm) with no deleterious effect on taste, color, smell or over all eating experience. In the case of small particle size additions, resulting foodstuffs had a creamier texture. In the case of large particle size additions, resulting foodstuffs had a firmer texture characterized by larger particles which required more mastication before swallowing. Taste tests showed that acceptable food products where produced at all tested loading and size distribution levels.

Example 19: MK7 Jerky

*Fusarium oxysporum* strain MK7 biomat, produced as described above, was used to create mycojerky, similar in appearance and taste to meat jerkies (i.e. beef jerky, buffalo jerky, pork jerky, chicken jerky, turkey jerky, etc.). Moist biomats were steamed in a pot steamer at 97° C. for 0.5 hour, cooled to room temperature. Biomats where size reduced to a size consistent with that normally found in jerky products. Size reduced biomat pieces where in some cases seasoned for flavor and dehydrated in a Cuisinart dehydrator (model DHR-20) for 20-200 minutes with an average dehydration time being 40-120 minutes. Dehydration time is a function of the amount of biomass loaded into the dehydrator, distribution of biomats in the dehydrator which impacts air flow in the dehydrator, water content of biomats (average water content approximately 75%), room temperature and desired water content in the final product. Water content post dehydration varied between 8% and 12% depending on desired product characteristics. In some cases, perforating the biomass before dehydration produced a product that tore more readily into small pieces thereby easing consumption. Perforation of the biomass was performed by using a fork, knife or tenderizer tool which both perforated the biomass as well as disrupted the filament network such that it tore more easily. A large variety of spice mixtures (i.e. Cajun, cheese, soy, vinegar, herbs, sour cream & onion, liquid smoke, vegan meat flavors, etc.) where evaluated. Spice mixtures were evaluated both before dehydration and post dehydration. Those samples which were spiced before dehydration offered more taste and better adhered to the biomass than those which were treated after dehydration. The resulting jerkies all performed well in taste tests.

Example 20: Myco-Chips

*Fusarium oxysporum* strain MK7 biomat, produced as described above, were used to chips, similar in appearance and taste to potato chips or corn chips. Moist biomats were steamed in a pot steamer at 97° C. for 0.5 hour, cooled to room temperature. Biomats where size reduced to a size consistent with that normally found in chip products as well as highly processed into a paste and formed into a chip like geometry. Myco-chips where then put into a frying pan of hot oil (temperature app equal to 380° F.) until brown. Cooking times varied as a function of biomass geometry but cooked very fast, usually in under 15 seconds. Produced fried chips proved to be very palatable and capable of offering a wide variety of taste experiences dependent upon spices added to or coated upon the biomass pre-frying.

Example 21: Hermetically Sealed Bioreactor:Biomat

Pyrex® glass trays 12.7×17.8 cm as well as 100×15 mm Petri dishes are used as the base tray. The glass trays are loaded with 200 mL of feedstock mixed with liquid nutrient medium (if required) and inoculum. The trays are covered and sealed with the gas-permeable membrane that is attached to a plastic frame with an integrated rubber gasket. The sealing system provides an effective aseptic seal between the membrane and the glass trays and enables easy assembly as well as opening/closing of the reactor for sampling and harvesting purposes.

A suite of different gas permeable membrane materials with different, thicknesses, pore sizes and textures (surface roughness) are used as materials for the gas liquid interface. Initially, eight (8) polymeric materials are used including polypropylene, polyethylene, polytetrafluorethylene, polycarbonates, polyamides, polypyrrolones, poly(amidoamine) dendrimer composite and cellulose acetate (e.g., Specialty Silicone Products, Inc. Corporate Technology Park, N.Y.; Thermo-Fisher, Waltham, Mass.; Merck Millapore, Burlington, Mass.). Three pore sizes are used for the materials (0.2, 0.45, 1.0 μm) that facilitate gas transfer in addition to the direct diffusion of gasses through the polymers themselves while excluding microorganisms. Additionally, sterile-cloth-like materials with different rough surface textures and tortuous paths for gas diffusion are used. A large selection of such materials are commercially available from other corporate sources including 3M, Solvay, Ube Industry and Saint-Gobain.

To analyze and determine parameters for different environmental and mission conditions, tray reactors are fitted with sensors to monitor temperature, dissolved oxygen and pH as a function of depth across the tray. Ports for sensors and wires crossing membranes into the reactor are sealed with silicone, epoxy, and/or adhesives depending on the membrane material. Septa integrated into the membranes are used as sample ports for collecting liquid samples for analysis by GC-MS, ICP-MS, IC and total C/N. Standard as well as microelectrodes are used to measure pH and electron acceptor flux ($O_2$) in real time across the gas-permeable membrane and within the biomat at regular time intervals (e.g., 6, 12, 24, 36, 48 hours). The flux information is important for matching real-time metabolic demands with membrane gas permeability and the changing concentrations and distributions of electron donors (organics) and nutrients (inorganics) needed for optimal growth and feedstock conversion.

Example 22: Un-Instrumented Reactors

Un-instrumented reactors used for growth studies with fungal strain *Fusarium oxysporum* MK7 as a model filamentous organism. Strain MK7 is an extremophilic fungus that has been shown to thrive on a wide variety of feedstocks including human wastes, food wastes, cyanobacteria and algae biomass, and lignocellulosic materials. Strain MK7 biomats have also been shown to have tolerance to high urea levels (at least 26 g/L) as well as high dissolved organic carbon, and osmotic pressure (300 g/L glycerol).

The feedstocks tested include: 1) surrogate human urine as the primary source of nitrogen; 2) surrogate food waste (dog food) as the primary carbon source; and 3) plant material (lignocellulose) as an additional carbon source. All feedstocks are extensively analyzed for organic and inorganic constituents, pH, and biological oxygen demand. Surrogate human urine is prepared using a medium composition recommended by NASA scientists or other scientists involved in studying mission wastes.

The effectiveness of the different gas permeable membranes are measured by conducting comparative biofilm-biomat growth studies wherein different membranes are sealed onto the surface of trays and Petri dishes containing various feedstocks and MK7 inoculum. The membranes are in direct contact with the liquid phase and are the only avenue of gas exchange between the gas/vapor exterior environment and the biofilm-biomats/liquid medium. Reactors are destructively sampled to measure growth (dry biomass weight, biomat thickness) over time. Growth rates are compared to control trays with no membranes. A factorial experimental design consisting of feedstocks and membrane combinations is tested to provide the best match of feedstock and membrane. Additional variables, including initial feedstock pH and inorganic nutrient additions, is also evaluated. Further, the experiments track the viable bacterial cell counts from feedstocks as a function of time to quantify the disinfection kinetics linked to biomat growth.

Example 23

The best performing membrane/feedstock combinations are used for additional experiments. The flux of gasses through the selected gas permeable membranes is first quantified and modeled by abiotic experiments. The flux of $O_2$ from the vapor phase outside of the reactor into the liquid phase uses the initial slope method and is measured using dissolved oxygen probes and medium that is initially anoxic. The flux of carbon dioxide from a carbon dioxide saturated liquid phase into the vapor phase also uses the initial slope method and is measured by total inorganic carbon analysis and with pH probes (a measure of carbonic acid). The dissolved inorganic carbon phase is 0%, 0.5% and 5% carbon dioxide initially. The data is integrated into the moving front fungal growth models to develop more accurate parameters.

The best performing membrane/feedstock combinations observed are then used for detailed biotic optimization experiments aided by a fungal growth model. Both glass trays and Petri dishes are used. The smaller Petri dishes facilitate the intensive destructive sampling for biomass and liquid analyses over time. Creation of conditions wherein nearly all of the added carbon and nutrients are converted into biomass with minimal wastes are identified. Here, carbon and electron fluxes and reactor conditions are evaluated by measuring the biomass produced per electron donor and biomass produced per electron acceptor yields. The elemental composition of the biomass is measured using commercial services (e.g. Microanalysis Inc., Wilmington Del.) to complete the mass balances. Parameters of interest include volumes of the liquid phase and concentrations of available feedstock and nutrients (carbon substrate, nitrogen source, inorganic nutrients, oxygen). The resulting data is used in a moving front mathematical model of fungal mat growth that facilitates a quantitative comparison and ultimately optimization of growth conditions.

The invention claimed is:

1. A food product, comprising:

(a) filamentous fungal biomass, consisting essentially of fungal mycelium and being free of feedstock on which the filamentous fungal biomass was grown, wherein a protein content of the filamentous fungal biomass is at least about 46 wt. %; and (b) animal meat.

2. The food product of claim 1, wherein the filamentous fungal biomass has been subjected to a treatment to inactivate the viability of the filamentous fungal biomass.

3. The food product of claim 2, wherein the treatment is selected from the group consisting of heating, irradiation, steaming, and combinations thereof.

4. The food product of claim 1, wherein the filamentous fungal biomass makes up between about 10 wt. % and about 50 wt. % of the food material.

5. The food product of claim 1, wherein the filamentous fungal biomass comprises size-reduced particles derived from a filamentous fungal biomat produced by surface fermentation.

6. The food product of claim 5, wherein the size-reduced particles have been size-reduced from the biomat by a means selected from the group consisting of cutting the biomat, chopping the biomat, dicing the biomat, mincing the biomat, grinding the biomat, blending the biomat, sonicating the biomat, and combinations thereof.

7. The food product of claim 1, wherein the filamentous fungal biomass comprises particles having an average particle length of 0.05 mm to 500 mm, an average particle width of 0.03 mm to 7 mm, and an average particle height of 0.03 to 1.0 mm.

8. The food product of claim 7, wherein the average particle length is about 0.4 mm to about 500 mm and the average particle width is about 0.4 mm to about 7 mm.

9. The food product of claim 8, wherein the average particle length is about 4 mm to about 10 mm, the average particle width is about 1 mm to about 3 mm, and the average particle height is less than about 0.75 mm.

10. The food product of claim 8, wherein the average particle length is less than about 1.5 mm, the average particle width is less than about 1 mm, and the average particle height is less than about 0.75 mm.

11. The food product of claim 1, wherein the animal meat is selected from the group consisting of beef, chicken, pork, and fish.

12. The food material of claim 1, wherein the filamentous fungal biomass comprises at least one filamentous fungus selected from the group consisting of *Fusarium* strain MK7 (ATCC Accession Deposit No. PTA-10698), *Fusarium venenatum, Fusarium avenaceum, Neurospora crassa, Agaricus bisporus, Boletus edulis, Cantarellus cibarius, Calvatia gigantea, Cyclocybe aegerita, Ganoderma lucidum, Grifola frondosa, Morchella* spp., *Hypsizygus tessellatus, Hypsizygus ulmarius, Laetiporus* spp., *Lentinula edodes, Pleurotus eryngii, Pleurotus ostreatus, Pholiota microspora, Sparassis crispa*, and *Tuber* spp.

13. The food product of claim 1, wherein the fungal mycelium comprises aerial hyphae.

14. The food product of claim 1, further comprising at least one additive selected from the group consisting of flavors, spices, flavor enhancers, fats, fat replacers, preservatives, sweeteners, color additives, nutrients, emulsifiers, stabilizers, thickeners, pH control agents, acidulants, leavening agents, anti-caking agents, humectants, yeast nutrients, dough strengtheners, dough conditioners, firming agents, enzyme preparations, gases, and combinations thereof.

15. The food product of claim 14, wherein the at least one additive is selected from the group consisting of flavors, spices, flavor enhancers, and sweeteners.

16. The food product of claim 14, wherein the at least one additive comprises a spice mixture selected from the group consisting of a Cajun spice mixture, a cheese spice mixture, a soy spice mixture, a vinegar spice mixture, an herb spice mixture, a sour cream and onion spice mixture, a liquid smoke spice mixture, and a vegan meat spice mixture.

17. The food product of claim 14, made by a method comprising:

(a) contacting the filamentous fungal biomass, the animal meat, and the at least one additive; and (b) dehydrating the filamentous fungal biomass.

18. The food product of claim 1, wherein at least one of the filamentous fungal biomass and the animal meat has been subjected to tenderization.

19. The food product of claim 1, comprising all essential amino acids.

20. The food product of claim 1, wherein the filamentous fungal biomass is the source for at least about 25 wt. % of protein in the food material.

21. The food product of claim 1, wherein the filamentous fungal biomass and the animal meat are the only sources of protein in the food material.

22. The food product of claim 1, wherein the filamentous fungal biomass comprises particles having an average particle size of about 75 to about 120 microns.

23. The food product of claim 22, wherein at least about 5 wt % of the particles have a particle size of at least about 180 microns and at least about 5 wt % of the filamentous fungal particles have a particle size of less than about 75 microns.

24. The food product of claim 1, wherein the filamentous fungal biomass comprises all essential amino acids.

25. The food product of claim 1, wherein the filamentous fungal biomass has a fiber content of at least about 23 wt. %.

26. The food product of claim 1, wherein the filamentous fungal biomass has a lipid content of about 6 wt. % to about 11 wt. %.

27. The food product of claim 1, wherein the food product is selected from the group consisting of a burger, a sausage, a hot dog, a chicken nugget, bacon, and jerky and a fish filet.

28. A food product, comprising:

(a) filamentous fungal biomass, wherein the filamentous fungal biomass consists essentially of fungal mycelium and is free of feedstock on which the filamentous fungal biomass was grown; wherein the filamentous fungal biomass comprises at least about 46 wt. % protein; wherein the filamentous fungal biomass comprises fiber; and the filamentous fungal biomass has been subjected to a treatment selected from the group consisting of inactivation of viability, deactivation of enzymes, and combinations thereof;

(b) animal meat; and (c) at least one additive selected from the group consisting of flavors, spices, flavor enhancers, fats, fat replacers, preservatives, sweeteners, color additives, nutrients, emulsifiers, stabilizers, thickeners, pH control agents, acidulants, leavening agents, anti-caking agents, humectants, yeast nutrients, dough strengtheners, dough conditioners, firming agents, enzyme preparations, gases, and combinations thereof.

* * * * *